US009464021B2

(12) United States Patent
Mehta et al.

(10) Patent No.: US 9,464,021 B2
(45) Date of Patent: Oct. 11, 2016

(54) METHOD OF PREPARATION OF STEREOSPECIFIC QUINONE DERIVATIVES

(71) Applicants: Dilip S. Mehta, Mumbai (IN); Priya Mohan, Lubbock, TX (US); Mayank Shastri, Lubbock, TX (US); Ted Reid, Lubbock, TX (US)

(72) Inventors: Dilip S. Mehta, Mumbai (IN); Priya Mohan, Lubbock, TX (US); Mayank Shastri, Lubbock, TX (US); Ted Reid, Lubbock, TX (US)

( * ) Notice: Subject to any disclaimer, the term of this patent is extended or adjusted under 35 U.S.C. 154(b) by 0 days.

(21) Appl. No.: 14/530,250

(22) Filed: Oct. 31, 2014

(65) Prior Publication Data
US 2015/0126763 A1 May 7, 2015

Related U.S. Application Data

(60) Provisional application No. 61/962,169, filed on Nov. 1, 2013.

(51) Int. Cl.
| | | |
|---|---|---|
| C07C 69/76 | (2006.01) | |
| C07C 46/00 | (2006.01) | |
| C07C 69/734 | (2006.01) | |
| C07C 41/18 | (2006.01) | |
| C07D 339/08 | (2006.01) | |
| C07C 45/56 | (2006.01) | |
| C07C 46/02 | (2006.01) | |
| C07C 69/618 | (2006.01) | |

(52) U.S. Cl.
CPC .............. *C07C 46/00* (2013.01); *C07C 41/18* (2013.01); *C07C 45/567* (2013.01); *C07C 46/02* (2013.01); *C07C 69/618* (2013.01); *C07C 69/734* (2013.01); *C07D 339/08* (2013.01)

(58) Field of Classification Search
CPC ..... C07C 41/18; C07C 45/567; C07C 46/02; C07C 43/215; C07C 49/255; C07C 50/14; C07C 46/00; C07C 69/618; C07C 69/734; C07D 339/08
See application file for complete search history.

(56) References Cited

U.S. PATENT DOCUMENTS

| | | |
|---|---|---|
| 4,199,531 A | 4/1980 | Kato |
| 4,603,223 A | 7/1986 | Hoffmann-LaRoche |
| 4,818,441 A * | 4/1989 | Imada .................... C07C 41/26 552/299 |

FOREIGN PATENT DOCUMENTS

| | | |
|---|---|---|
| GB | 2055097 | 6/1983 |
| WO | WO 2010/034999 | 4/2010 |
| WO | WO 2011/117324 | 9/2011 |

OTHER PUBLICATIONS

Xiong-Jie et al. (Synthetic Studies on Coenzyme Q10 Part 1 An Efficient and Highly Stereocontrolled Synthesis of Coenzyme Q10 via a C5+C45 Strategy, Helvetica Chimica ACTA—vol. 88, pp. 2575-2581 2005).*
European Search Report and Written Opinion, dated Feb. 26, 2015, for App No. 14191331.9—EP2868658.
Okamoto K Et Al: "Synthesis of Quinones Having Carboxy- and Hydroxy-Alkyl Side Chains, and Their Effects on Rat-Liver Lysosomal Membrane", Chemical and Pharmaceutical Bulletin, Pharmaceutical Society of Japan, JP, vol. 30, No. 8, Aug. 1, 1982, pp. 2797-2819, XP000674670, ISSN:0009-2363 * Comp.XIIIa and XIIIc in Chart 2 on p. 2798 *.
Xiong-Jie Yu et al: "Synthetic Studies on Coenzyme Q10", Helvetica Chimica ACTA, vol. 88, No. 10, Oct. 28, 2005, pp. 2575-2581, XP055172013, ISSN: 0018-019X, DOI:0.1002/hlca. 200590197 * Comp.6 in the Scheme on p. 2577; p. 2576, paragraph 5 *.

* cited by examiner

*Primary Examiner* — Yevegeny Valenrod
*Assistant Examiner* — Blaine G Doletski
(74) *Attorney, Agent, or Firm* — Locke Lord LLP; Bryan D. Zerhusen

(57) ABSTRACT

The description provides processes for the regio and stereospecific synthesis of polyprenylatedquinone derivatives, such as Vitamin K1, K2 and Ubiquinone, exploiting dithioacetals, especially 1,3-dithiane, mediated Umpolung chemistry which works along a new concept "Inhibiting resonance delocalization (IRD)" to overcome isomerization generated due to delocalization of allyliccarbanion on the π-electron cloud of an allylic systems by the conventional synthesis.

2 Claims, 4 Drawing Sheets

1st Step: Generation of Carbocation

2nd Step: Resonance delocalization

3rd Step: Electrophilic substitution reaction

2-[3-(1,4-Dimethoxy-3-methyl-naphthalen-2-yl)-1-methyl-propenyl]-[1,3]dithiane

Ia 4-(1,4-Dimethoxy-3-methyl-naphthalen-2-yl)-2-methyl-but-2-enoic acid ethyl ester IIa 2-[1-Methyl-3-(2,3,4,5-tetramethoxy-6-methyl-phenyl)-propenyl]-[1,3]dithiane Ib 2-Methyl-4-(2,3,4,5-tetramethoxy-6-methyl-phenyl)-but-2-enoic acid ethyl ester IIb

METHOD OF PREPARATION OF STEREOSPECIFIC QUINONE DERIVATIVES

CROSS-REFERENCE TO RELATED APPLICATIONS

Under 35 U.S.C. §119(e) this application claims the benefit of U.S. Provisional Application No. 61/962,169, filed Nov. 1, 2013 titled: Method of Preparation of Stereospecific Quinone Derivatives, which is hereby incorporated by reference in their entirety for all purposes.

FIELD

The present disclosure relates to regio- and stereospecific synthesis of quinone derivatives, attached with polyprenyl side chain, to yield various natural equivalent vitamins, e.g., vitamin K and ubiquinone.

SUMMARY

Current knowledge of stereochemistry demands responsible drug development. Most proteins, nucleic acids, polysaccharides, lipids and steroids are chiral. In other words, almost all of the main therapeutic targets are chiral and, therefore, show stereospecific interactions with endogenous and exogenous ligands. Stereo selectivity of interaction is a well-recognized criterion of specific drug-receptor interactions. Such stereoselectivity has been observed with all classes of receptors, with both physiological and non-physiological ligands. However, pharmacological implications of this have not always been appreciated, especially the toxicity aspects.

It is not always possible to determine the long term toxic effects of the minor quantities of unintended isomers in a product by conventional acute and chronic toxicity studies. This minor quantum of unintended isomers may not reveal their real character in the short period of the chronic toxicity study. It is particularly important to consider this fact for those compounds (drugs) which are likely to be administered for a lifetime.

Therefore, when there is a possibility of multiple isomers in synthesizing a drug compound it is ideal to have a synthetic protocol yielding a single active isomer of the natural equivalent. In case the synthesized drug is a mixture of isomers, it has been recommended by various drug authorities, that each isomer besides the known active natural equivalent isomer should be segregated in pure form and their toxicity profile investigated. For example, the FDA recommends, in case of technology limitations in the production of a single isomer, to have a toxicological profile of each unintended isomer in the commercial product, in order for marketing approval.

Resolution of individual chiral compounds is a daunting task. For example, vitamin K2-7 has 64 possible isomers and this number enlarges as one proceeds to physiologically active vitamin K2-8 with 128 isomers and vitamin K2-9 with 256 possibilities. However, a number of advantages stem from using stereochemically pure drugs, including potentially reducing the total dose required, simplification of the dose-response relationship, a source of inter-object variability is removed, and toxicity from the inactive stereoisomer(s) is minimized or eliminated. Accordingly, the use of only the active isomer as therapeutic agent may yield several benefits.

Based on our current knowledge of isomeric toxicity, efficacy, bioavailability, clearance and other biological properties, it is desirable to produce a single isomer for biologically active pharmacologic agents. In particular, because of the commercial importance of the vitamin K series, and quinone compounds as well as their derivatives, e.g., ubiquinone or Coenzyme Q10, a need exist in the art for methods of synthesizing optically or stereochemically pure isomers.

SUMMARY

The description provides processes for the regio and stereospecific synthesis of polyprenylatedquinone derivatives, such as Vitamin K1, K2 and Ubiquinone, exploiting dithioacetals, especially 1,3-dithiane, mediated Umpolung chemistry which works along a new concept "Inhibiting resonance delocalization (IRD)" to overcome isomerization generated due to delocalization of allylic-carbanion on the π-electron cloud of an allylic systems by the conventional synthesis.

In certain aspects, processes for synthesis of all-trans vitamin K1, K2 and Ubiquinone is described. In certain embodiments, the synthesis is achieved by a method of coupling of a quinone group with a polyprenyl side chain where either of the two moieties may have 1,3-dithiane as a terminal group while undergoing umpolung chemistry. Similarly while coupling two polyprenyl fragments to each other in building of the all-trans side chain. A stereospecific synthesis of vitamin K-1 is also achieved along the same synthetic outline using a hexahydro chiral farnesyl derivative retaining optical and geometrical isomeric properties equivalent to that of the natural K1.

In certain embodiments, the description provides a method for synthesis of polyprenylated quinone derivatives comprising regiospecific and stereospecific synthesis of compound of formula I:

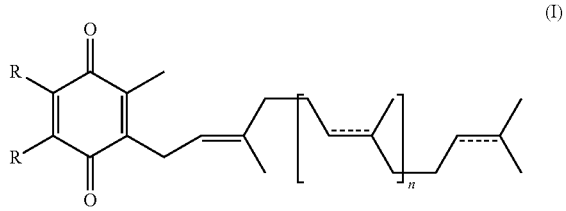

(I)

wherein n=an integer from 0 to 8,
R=is independently selected from —CH=CH—CH=CH— and OCH3; and
the said method comprising the steps of providing a dithioacetal derivative selected from the group of quinones (II), prenols (V) and combinations thereof,

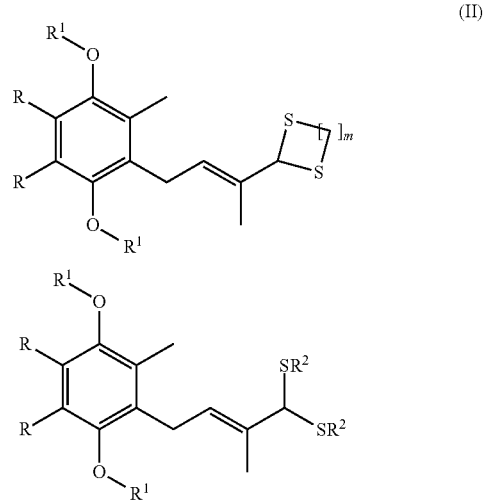

(II)

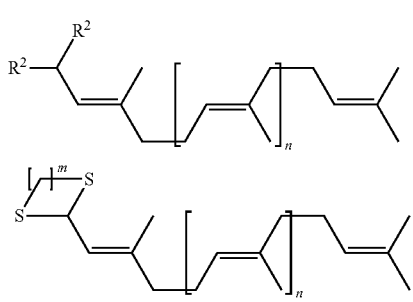

(V)

wherein m=2 or 3;
n=is an integer from 0 to 8;
R=—CH=CH—CH=CH— or OCH$_3$
R$^1$=CH$_2$OCH$_3$, TMS, TBS, Acetyl, Benzyl, or PMB; and
R$^2$=Et or Ph;
the said derivatives participating in a reaction with halides of respective counter synthon of formula III or IV,

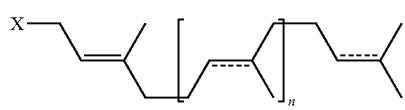

(III)

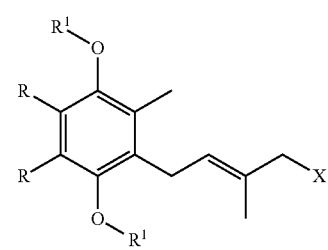

(IV)

wherein R=—CH=CH—CH=CH— or OCH$_3$;
R$^1$=CH$_2$OCH$_3$, TMS, TBS, Acetyl, Benzyl, or PMB; and
X=OMs, Br, Cl, I, OTs.

In certain additional embodiments, the quinone derivatives are selected from the group consisting of coenzyme Q10, vitamin K1, vitamins K2-4, K2-6, K2-7, K2-8 and K2-9.

In an additional aspect, the description provides compounds as described herein, including therapeutic compositions comprising effective amounts of the same, and optionally a pharmaceutically acceptable carrier or excipient.

In certain embodiments, the description provides compounds of formula VI:

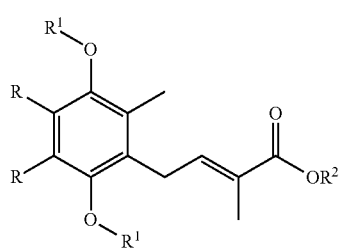

(VI)

wherein R=—CH=CH—CH=CH— or OCH$_3$;
R$^1$=CH$_2$OCH$_3$, TMS, TBS, Acetyl, Benzyl, or PMB; and
R$^2$=ethyl, methyl, t-butyl, benzyl;

the said compound ascertains the regiospecificity and trans-stereospecificity of unsaturation present at β, γ position with respect to aromatic core.

In certain additional embodiments, the description provides a synthon compound of formula VII:

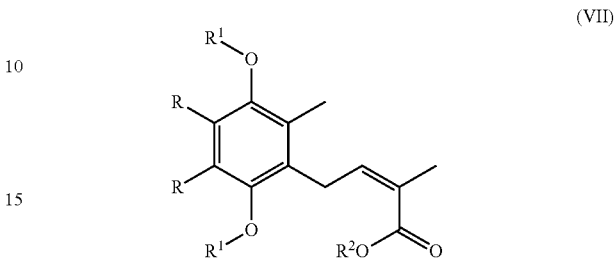

(VII)

wherein R=—CH=CH—CH=CH— or OCH$_3$;
R$^1$=CH$_2$OCH$_3$, TMS, TBS, Acetyl, Benzyl, or PMB; and
R$^2$=ethyl, methyl, t-butyl, benzyl;

the said compound ascertains the regiospecificity and trans-stereospecificity of unsaturation present at β, γ position with respect to aromatic core.

Where applicable or not specifically disclaimed, any one of the embodiments described herein are contemplated to be able to combine with any other one or more embodiments, even though the embodiments are described under different aspects of the invention.

The preceding general areas of utility are given by way of example only and are not intended to be limiting on the scope of the present disclosure and appended claims. Additional objects and advantages associated with the compositions, methods, and processes of the present invention will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present invention. The publications and other materials used herein to illuminate the background of the invention, and in particular cases, to provide additional details respecting the practice, are incorporated by reference, and for convenience are listed in the appended bibliography.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which.

DETAILED DESCRIPTION

Figure 1:
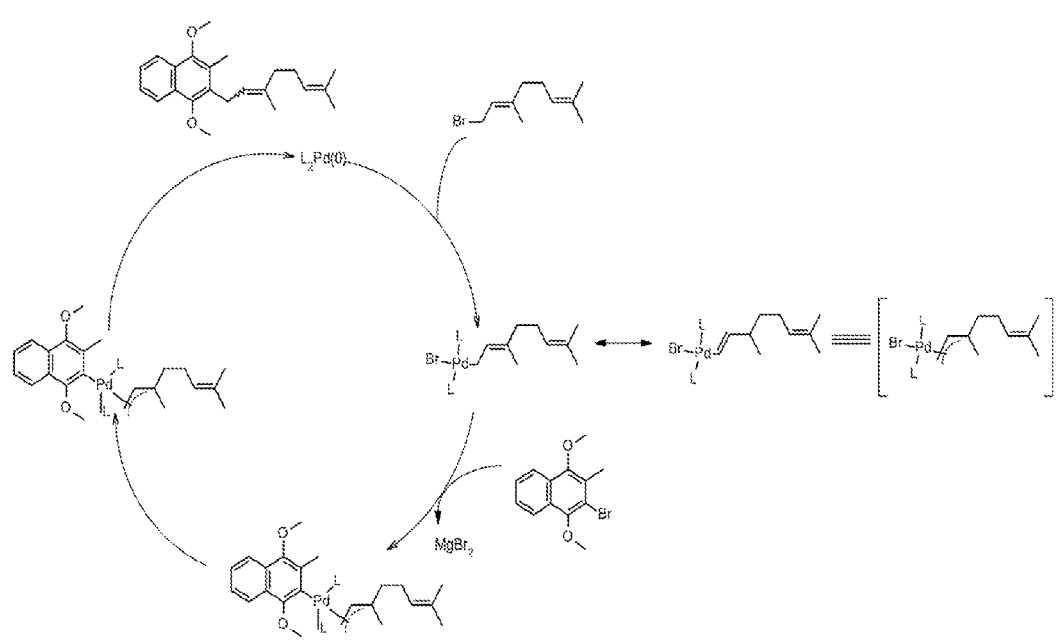
FIG. 1: Mechanistic study of Kumada coupling.

Importance of stereochemistry in human physiology has been well documented. The enormous impact of a stereochemically diverse compound on human physiology, of an otherwise well tolerated and useful drug substance, is scattered throughout the drug and non-drug history. This led us to closely examine the stereochemistry of synthetically produced polyprenylated quinone derivatives in human consumption. Our finding was that the synthetic procedures deployed to produce these derivatives have not been successful in producing the natural equivalent and that there was a clear need for improvement to achieve the natural equivalent polyprenylated quinone derivatives with higher yields. Inventors have devised novel synthetic methods to bridge this inadequacy.

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

It should also be understood that, unless clearly indicated to the contrary, in any methods claimed herein that include more than one step or act, the order of the steps or acts of the method is not necessarily limited to the order in which the steps or acts of the method are recited.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

The term "about" or "approximately" means an acceptable error for a particular value as determined by one of ordinary skill in the art, which depends in part on how the value is measured or determined.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the 10 United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The present disclosure relates to the regio and stereospecific synthesis of prenylated all-trans quinone derivatives and particularly the sub-group of vitamins and ubiquinone. The presence of cis-isomers in varying amount in commercially available vitamin K2-7 and other K vitamins is a matter of concern with the unpredictability of cis-isomer physiology, their being new chemical entities for human use, taking cognizance of the fact that nature makes only the all-trans form of these vitamins. None of the existing literary work on these molecules presents a plausible synthetic strategy to afford quinone derivative of the all-trans polyprenyl side chain. The extent of the presence of cis-isomer, in synthetically derived prenylated quinone derivatives, largely depends upon: a) the chemistry adapted to couple the side chain onto the quinone derivative; and b) the method applied to attach two prenyl building blocks.

The current application is a process patent for the synthesis of all-trans forms of quinone derivatives in general and specifically that of Coenzyme Q10 and vitamin K series and more specifically vitamin K1, K2-4 and K2-6, K2-7, K2-8 and K2-9. These all-trans forms are achieved through the discovery of novel synthons and chemical pathways which preclude the use of column chromatography, toxic catalysts and reagents. This methodology also excludes formation of isomers other than the predetermined one, particularly that of natural equivalent such as all-trans which are the only ones acceptable for human needs.

The need for all-trans quinone derivatives with polyprenyl side chains, i.e. equivalent to natural products, arises out of the toxicity lessons learned in drug development history. At the roots of the 1938 Federal Food, Drug and Cosmetics act is the elixir sulfanilamide and other similar disasters. A great example is Thalidomide, in the 1950s, which was the reason for thousands of babies born with severely deformed limbs and other malformations. This is described as the greatest drug disaster ever. However, the U.S. FDA did not permit the use of thalidomide, and its rigorous testing and high standards protected the American public from this drug disaster. Thalidomide is a classic example of the vastly diverse effects of stereochemistry on human physiology. It is generally believed that most, if not all, of the teratogenicity associated with the drug thalidomide is attributable to the R(−)-isomer.

In nature, very little is symmetrical. Indeed, most of nature is chiral, including the human body. Most proteins, nucleic acids, polysaccharides, lipids and steroids are chiral. In other words, almost all of the main therapeutic targets are chiral and, therefore, show stereospecific interactions with endogenous and exogenous ligands [1]. Stereo selectivity of interaction is a well-recognized criterion of specific drug-receptor interactions. Such stereo selectivity has been observed with all classes of receptors, with both physiological and non-physiological ligands. However, pharmacological implications of this have not always been appreciated, especially the toxicity aspects.

It is not always possible to determine the long term toxic effects of the minor quantities of unintended isomers in a product by conventional acute and chronic toxicity studies. This minor quantum of unintended isomers may not reveal their real character in the short period of the chronic toxicity study. It is particularly important to consider this fact for those compounds (drugs) which are likely to be administered for a lifetime. Therefore, with our current knowledge of isomeric toxicity, efficacy, bioavailability, clearance and other biological properties, it is desirable to produce a single isomer, such as in the case of Coenzyme Q10 and the vitamin K series. The FDA recommends, in case of technology limitations in the production of a single isomer, to have a toxicological profile of each unintended isomer in the commercial product, in order for marketing approval.

Agranat et al state that "Likely advantages of using stereochemically pure drugs are that: (1) the total dose could be reduced, (2) the dose-response relationship would be simpler, (3) a source of inter-object variability would have been removed and (4) toxicity from the inactive stereoisomer would be minimized.". Thus the use of only the active isomer as therapeutic agent may yield several benefits.

Further, some of the stunning examples of effects of stereochemistry to human physiology are:

Toxicity:

Thalidomide: the S-enantiomer is a teratogen, the R-enantiomer is a sedative.

Ketamine: the S-enantiomer is an anesthetic, the R-enantiomer causes hallucinations.

Ethambutol: the S-enantiomer is tuberculostatic, the R-enantiomer is associated with blindness [6,7].

Penicillamine: the S-enantiomer is antiarthritic, the R-enantiomer is a mutagen.

Efficacy:

S-ibuprofen is over 100-fold more potent an inhibitor of cyclo-oxygenase I than R-ibuprofen.

R-methadone has a 20-fold higher affinity for the µ opioid receptor than S-methadone.

S-citalopram is over 100-fold more potent an inhibitor of the serotonin reuptake transporter than R-citalopram.

Bioavailability and Clearance:

The bioavailability of R-verapamil is more than double that of S-verapamil due to reduced hepatic first-pass metabolism.

The clearance of R-fluoxetine is about four times greater than (5)-fluoxetine due to a higher rate of enzyme metabolism.

The volume of distribution of R-methadone is double that of S-methadone due to lower plasma binding and increased tissue binding.

Matschiner and Bell reported evidence of differential biological activity of the two geometric isomers of phylloquinone. This investigative study reports "The results reported here suggest that cis-phylloquinone has little or no biological activity as vitamin K. The trans isomer appears to have the full potency of the vitamin" and further states that "The data in table 1 indicate a significant difference in hepatic retention of the two isomers." and "From these data it appears that the cis isomer is retained preferentially by mitochondria while the biologically active trans isomer is associated principally with the microsomal fraction and subfractions. The rough membrane fraction of the microsomes, derived principally from the rough endoplasmic reticulum is particularly rich in the trans isomer."

The advance described herein is based on a specially designed five carbon side chain quinone building block, which has certain advantages. Natural chains such as farnesyl and solanesyl can directly attach to such a building block and deliver vitamin K2-4 and CoQ10. Also such a quinone building block preserves the all-trans character of the alpha position. Preparation of vitamin K2-7 would need an all-trans hexaprenyl chain which requires a new approach. Here we describe a novel approach to achieve the all-trans quinone derivatives of the vitamin K1, K2 series and CoQ series.

In certain aspects, processes for synthesis of all-trans vitamin K1, K2 and Ubiquinone is described. In certain embodiments, the synthesis is achieved by a method of coupling of a quinone group with a polyprenyl side chain where either of the two moieties may have 1,3-dithiane as a terminal group while undergoing umpolung chemistry. Similarly while coupling two polyprenyl fragments to each other in building of the all-trans side chain. A stereospecific synthesis of vitamin K-1 is also achieved along the same synthetic outline using a hexahydro chiral farnesyl derivative retaining optical and geometrical isomeric properties equivalent to that of the natural K1.

In certain embodiments, the description provides a method for synthesis of polyprenylated quinone derivatives comprising regiospecific and stereospecific synthesis of compound of formula I:

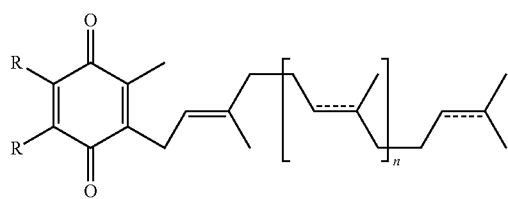

(I)

wherein n=an integer from 0 to 8,
R=is independently selected from —CH=CH—CH=CH— and OCH3; and
the said method comprising the steps of providing a dithioacetal derivative selected from the group of quinones (II), prenols (V) and combinations thereof,

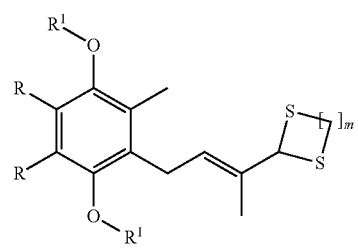

(II)

-continued

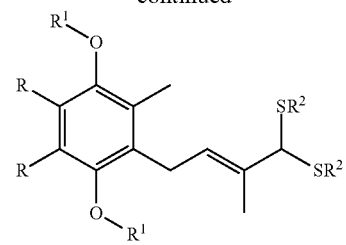

(V)

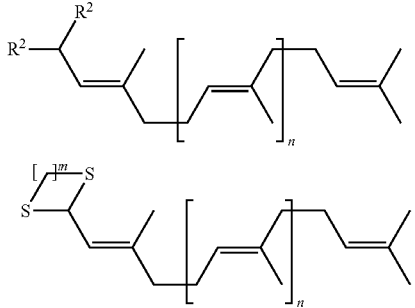

wherein m=2 or 3;
n=is an integer from 0 to 8;
R=—CH=CH—CH=CH— or $OCH_3$
$R^1$=$CH_2OCH_3$, TMS, TBS, Acetyl, Benzyl, or PMB; and
$R^2$=Et or Ph;
the said derivatives participating in a reaction with halides of respective counter synthon of formula III or IV,

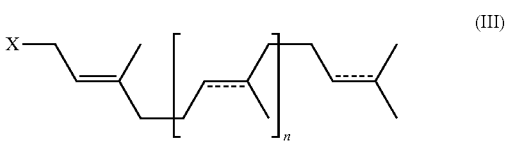

(III)

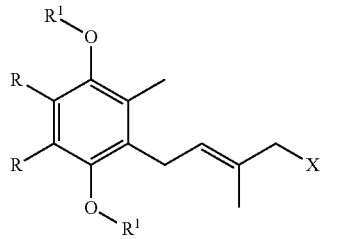

(IV)

wherein R=—CH=CH—CH=CH— or $OCH_3$;
$R^1$=$CH_2OCH_3$, TMS, TBS, Acetyl, Benzyl, or PMB; and
X=OMs, Br, Cl, I, OTs.

In certain additional embodiments, the quinone derivatives are selected from the group consisting of coenzyme Q10, vitamin K1, vitamins K2-4, K2-6, K2-7, K2-8 and K2-9.

In an additional aspect, the description provides compounds as described herein, including therapeutic compositions comprising effective amounts of the same, and optionally a pharmaceutically acceptable carrier or excipient.

In certain embodiments, the description provides compounds of formula VI:

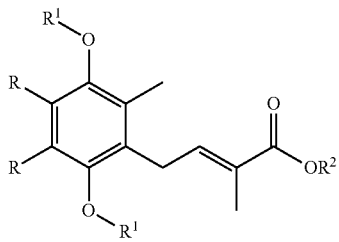

(VI)

wherein R=—CH=CH—CH=CH— or OCH$_3$;
R$^1$=CH$_2$OCH$_3$, TMS, TBS, Acetyl, Benzyl, or PMB; and
R$^2$=ethyl, methyl, t-butyl, benzyl;
the said compound ascertains the regiospecificity and trans-stereospecificity of unsaturation present at β, γ position with respect to aromatic core.

In certain additional embodiments, the description provides a synthon compound of formula VII:

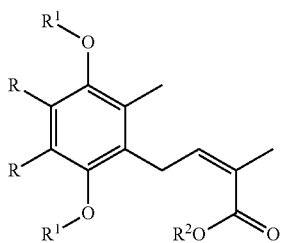

(VII)

wherein R=—CH=CH—CH=CH— or OCH$_3$;
R$^1$=CH$_2$OCH$_3$, TMS, TBS, Acetyl, Benzyl, or PMB; and
R$^2$=ethyl, methyl, t-butyl, benzyl;
the said compound ascertains the regiospecificity and trans-stereospecificity of unsaturation present at β, γ position with respect to aromatic core.

Without being bound by any particular theory, the inventors hypothesized that two major factors affected the stereospecific synthesis of vitamin K2 series and CoQ series: i) the chemistry adapted to couple the side chain on to the quinone derivative; and ii) the method applied to attach the two prenyl building blocks.

Current methods for synthesis of prenylated quinone derivatives, such as vitamin K-1, K2-4 and K2-7, mostly start with hydroxy quinone with further modification of the hydroxyl group to a choice of protecting group such as methoxy, ethoxy, methoxy methyl, benzyl, t-butyl silyl, t-butyl dimethyl silyl, acetoxy etc. This starting block of prior art, thus needs to couple with either a phytol, a tetraprenyl, a heptaprenyl, or a decaprenyl side chain, to meet the target of synthesizing vitamin K1, K2-4, K2-7 and ubiquinone respectively. Alternately, first a smaller chain is attached to the quinone compound and then it is further built-up to the target length. In either case two processes are involved, firstly, a) C—C coupling reaction to attach a side chain to a quinone derivative and, secondly, b) attachment of two prenyl chains where both of them may be in segmental form or one of them may, at one end, already be attached to a quinone derivative. Hence there are two types of chemical coupling requirements a) C—C Coupling Reactions and b) Prenyl Chains Coupling. Below we review the classes of chemical reactions applied to achieve C—C coupling and attachment of prenyl chains and difficulties associated with these procedures in maintaining stereospecificity.

For example, coupling reactions such as Negishi, Kumada, Suzuki and others to couple a side chain with a quinone derivative as mentioned in various patents and scientific articles. In general, coupling reactions such as Negishi, Kumada, Suzuki and others have been utilized to enforce a C—C bond formation between the quinone derivative and prenyl side chain, however most of these chemical transformations suffer with significant loss of stereoselectivity. Such a strategy doesn't install the polyprenyl side chain with absolute retention of stereochemistry. Most of these coupling reactions proceed via formation of a π-allyl palladium complex after the oxidative addition of prenyl halide with Pd (0) which accounts for the occurrence of cis-trans isomerization (FIG. 1). Formation of these n-allyl complexes is a routine process found in coupling reactions utilizing Ni, Pd, Sn and other transition element based catalysts. There was a need for chemistry that would overcome this loss and provide a robust methodology to produce the desired compound with commercially significant yields.

As shown in FIG. 1, depicting the mechanistic pathway, prenyl halide (b) takes part in oxidative addition with a Pd(0) complex to form a Pd(II) complex (c), which generates a n-allyl complex (e). Resonance delocalization occurs in this complex which accounts for the loss of a stereospecific outcome. However, complex (e) participates in transmetalation with dimethoxynaphthyl Grignard reagent (f) to provide (g) that undergoes cis-trans isomerization to yield complex (h), which eventually produce coupled product (i) and regenerates the catalyst.

Many patents have used Kumada or Suzuki and other such chemistry for coupling the polyprenyl side chain to the aromatic quinone derivatives. Kumada and Suzuki techniques were devised to couple an aromatic moiety with an allylic chain. This has worked well and has been adapted to couple a polyprenyl chain to a quinone moiety to obtain vitamin K2. The limitation of using Kumada or Suzuki coupling becomes evident when a stereoisomer is coupled by these techniques.

Patent application WO 2010/034999 A1 (page 3, lines 22-27) states "The present inventors have devised a synthetic strategy for the formation of MK-7 in solid, especially, crystalline form. The inventors have therefore provided the first solid form of this compound. No-one before has achieved the synthesis of MK-7 as a solid. The method utilizes Kumada chemistry to connect a short 2-isoprenoid side chain to a nephthaquinone ring. The rest of the MK-7 side chain is then built up on the formed compound using Bielmann chemistry." They further state that (page 4, lines 3-4) "The process devised by the inventors is remarkable in that no Z isomers are formed leading to a solid product previously unknown in the art." It is possible to have a solid product of a multi-isomeric MK-7 and such a product has been approved by EU Novel Foods (>5%-cis, >2% unidentified impurities (see point 6, page 2 of http://www.food.gov.uk/multimedia/pdfs/acnfp1045synvitk2, September 2013), however, "a no Z isomer" is difficult to explain considering the generation of a π-allyl palladium complex occurring in Kumada and Biellmann chemistry as explained.

Figure 2:
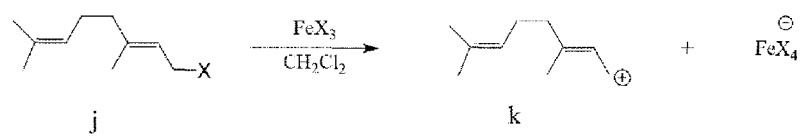
FIG. 2. Friedel-Craft prenylation of dimethoxy naphthalene.
Figure 2:
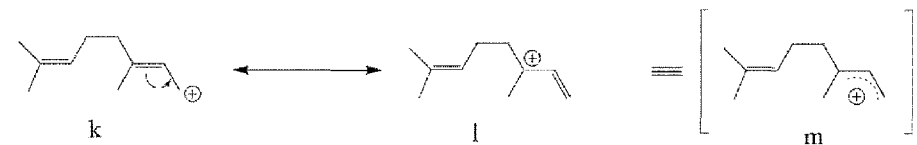
Figure 2:
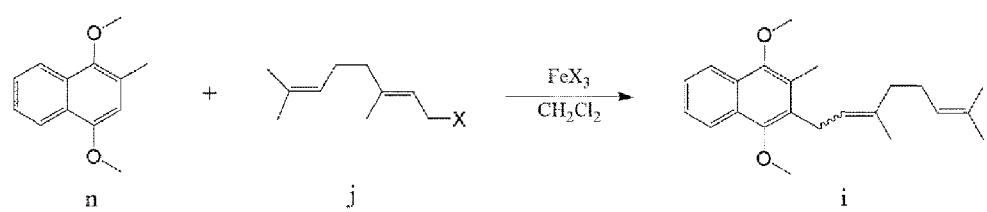

Friedel-Craft prenylation of dimethoxy naphthalene. Besides these coupling reactions, Friedel-Craft reaction has also been applied to attach the polyprenyl side chain to the quinone derivatives (e.g., dimethoxy naphthalene) without success in preventing the loss of stereochemistry. The loss of stereochemistry during the course of reaction is explained by the generation of allyl carbocation. A classic Friedel-Craft reaction resumes with generation of allylic carbocation (k), which undergoes delocalization that explains the observed stereo selectivity loss during the chemical transformation (FIG. 2). Generated allylic carbocation involves an electrophilic aromatic substitution reaction to create the desired product (i) with compromised stereo-control.

The majority of Lewis acids such as ZnCl2, AlCl3, BF3.Et2O, SnCl4, FeCl3, TiCl4 are reported to carry out such transformations with varying amounts of unintended isomers. An effort towards the stereoselective addition of a monoprenyl subunit containing terminal a sulfonyl group, a key component towards the synthesis of vitamins and coenzyme Q series, was made utilizing the Friedel-Craft reaction. However, most of these chemical transformations carried out in presence of various Lewis acids suffer from poor yield and poor stereoselectivity.

Yet another common approach has been to use the concept of creating an adduct of menadione with cyclopentadiene. This approach has the merit of retaining regiospecificity. Referring to the U.S. Pat. No. 4,603,223, the inventors of the said patent state that E configuration of the coupled chain, besides being regiospecific, also nearly retains stereo integrity. Referring to the same patent (page 3, lines 42-46) inventors state "Thus, for example, when a compound of formula II is used in the pure (E)-form, there can be obtained the corresponding compounds of formulae IV and V in practically pure (E)-form." In Example 7, though they start with all (E) polyprenyl side chain, the resulted product has HPLC purity of only 95.6% all-trans isomer. Emergence of the varying quantum of cis isomer is noticed even when pure trans prenyl chain was used as a starting material. Further, analyzing the data of the examples presented in this patent, this method shows low yield. The present inventors have approached the problem with a view to remove the "practically pure," and low yield limitations.

Figure 3:
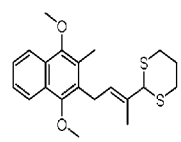
FIG. 3. Novel synthons essential for stereospecific synthesis of polyprenylated quinone derivatives.
Figure 3:
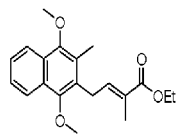
Figure 3:
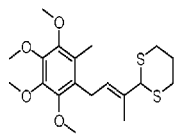
Figure 3:
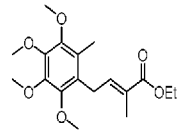

The present description provides processes and compounds that overcome one or more of the drawbacks of the above reviewed approaches in achieving a commercially robust process with regiospecificity, which results in high yield and required stereo purity. In particular, as described herein a strategy is provided, which includes creating novel synthons (FIG. 3. IIa,b) which convert to compounds (FIG. 3. Ia,b) consisting of monoprenyl subunits having 1,3-dithiane at the terminal position, a non-obvious choice in extending a side chain without formation of any unintended isomers. The possibility of constructing compounds (FIG. 3. IIa,b) in absolute trans and cis geometrical form, allow access to pure trans and when intended cis isomers of vitamin K1, K2-4, K2-7 and ubiquione.

The stereospecificity of K vitamins and coenzyme Q depends on the stereospecificity of the side chain to be attached to the aromatic moiety. Hence, synthesis of higher homologues of prenol in a stereospecific manner holds the key to the successful stereospecific synthesis of these molecules. There is a paucity of stereospecific precedence to attach two prenyl building blocks. Most of the reports available utilizes Biellmann chemistry, using aromatic a sulfonyl stabilized anion to combine other prenyl building blocks having a leaving group intact, which endures a mixture of isomers predominantly trans along with cis-isomer in varying proportion.

Application of a sulfone stabilized anion to participate in Biellmann chemistry is an important synthetic tool to facilitate C—C bond formation; however it suffers the loss of stereospecificity in case of an allylic or prenyl system (Exemplary Scheme 1).

Firstly, Step 1, we adapted a HornerWadsworth-Emmons (HWE) olefination reaction to obtain the β,γ-unsaturated double bond with absolute trans-geometry. We envisioned a novel compound (FIG. 3. Ia,b) serving our purpose in not only retaining the absolute trans-geometry but also in providing a synthetic tool to extend the prenyl side chain to yield vitamin K2-4, K2-7, K-1 and CoQ-10. Next, Step 2, to prepare vitamin K2-7, was the preparation of hexaprenyl-bromide, which further on, Step 3, was coupled with the already prepared dithiane compound (FIG. 3. Ia). These three steps are detailed below. Later we will review the preparation of vitamin K2-4, vitamin K1, CoenzymeQ10 and other prenylated quinone derivatives.

Scheme 1: Application of Biellmann Chemistry to Synthesize Higher Homologue of Prenol.

Figure 4:
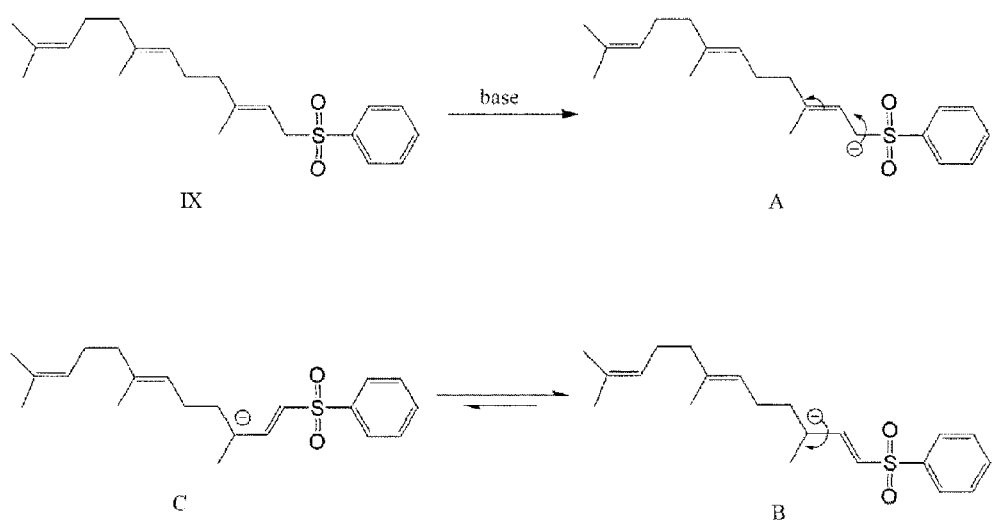
FIG. 4. Illustrates the loss of stereoselectivity through Biellmann chemistry to synthesize higher homologue of prenol. The carbanion has a pronounced tendency to hybridize to an sp2 hybridization and participate in resonance hybridization. Rotation of the bond occurs, accounting for the cis-trans isomerization observed in the coupled product.

Referring to FIG. 4, the loss of stereoselectivity of the coupled product can be explained by the resonance stabilization of the allylic carbanion. Here this carbanion has a pronounced tendency to hybridize to an sp2 hybridization and participate in resonance hybridization. Rotation of the bond occurs, accounting for the cis-trans isomerization observed in the coupled product.

Origins of Biellmann attachments and C—C bond formation were not with a specific view of stereo compounds in mind, but a general procedure to attach two organic fragments, one bearing an aromatic sulfonyl moiety and the other containing a leaving group. The variability of the stereoselectivity of the polyprenyl side chain obtained by this chemistry hugely depends upon the kind of aromatic sulphonyl linker being used e.g. p-toluenesulfinyl, benzenesulfonyl, thiophenolate etc. but this stereoselectivity never reaches the heights of stereospecificity.

An analysis of this problem led us to conclude that to ensure stereospecificity in the attachment of two polyprenyl fragments there was a need to utilize a group that could hinder the delocalization of the anion. This is a novel strategy in the quinone derivatives chemistry to provide an all-trans synthetic K2.

Biellmann chemistry doesn't ensure the maintenance of all-trans character while attaching two all-trans polyprenyl side chains. Many utilize Biellmann chemistry to build polyprenyl side chains e.g. PCT publications WO 2011/117324 A2 and WO 2010/034999 A1.

The present investigators undertook extensive investigation to resolve the yet unsolved above-described problem of achieving a single active isomer synthesis in the conventionally-known processes and recent attempts to prepare all-trans vitamin K2-7 (WO 2010/034999 A1). Though some patent literature refers to an all-trans product (WO 2011/117324 A2), it is not demonstrated by examples. The stereo specificity of polyprenyl side chain synthesized by applying Biellmann chemistry is questionable. Coupling reactions such as Kumada, Suzuki, Negishi and others are very instrumental in C—C bond formation, however they do not ensure the absolute stereo specificity when applied in allylic or prenylic system due to delocalization of electrons on the π-electron cloud of double bond.

In the backdrop of the preceding understanding, the present inventors recognize the challenge posed by the isomeric spectrum of 8 isomers for vitamin K2-4 and a far greater propensity of 64 isomers in the case of vitamin K2-7. It is also important to note that commercial interest for K2-6, K2-8 and K2-9 along with that of vitamin K2-7 may become significant as more studies report the need for the presence of these vitamins in the natural mix. The present invention covers the stereospecific synthesis of all these vitamins in the all-trans form.

An all-trans composite side chain, prepared from commercially available all natural isoprenoid chains of a required length is a pre-requisite to synthesize an all-trans vitamin K series and ubiquinone. Exceptions to the requirement of a composite chain are Coenzyme Q10, vitamin K1 and vitamin K2-4 where a non-composite single natural side chain is sufficient with the use of novelquinone building blocks. These building blocks could be utilized to prepare vitamin K1, K2 and ubiquinone series products by attaching an all-trans side chain by adopting the new concept of "Inhibition of resonance delocalization (IRD). This invention is used for, but is not limited to, the synthesis of all-trans quinone derivatives such as coenzyme Q10, vitamin K1, Vitamins K2-4, K2-6, K2-7, K2-8 and K2-9.

Several novel synthons have been prepared en route to the target molecule. More in particular, the disclosure relates to a new intermediate building blocks 2-[3-(1,4-Dimethoxy-3-methyl-naphthalen-2-yl)-1-methyl-propenyl]-[1,3]dithiane and 2-[1-Methyl-3-(2,3,4,5-tetramethoxy-6-methyl-phenyl)-propenyl]-[1,3]dithiane, prepared from a novel building block 4-(1,4-Dimethoxy-3-methyl-naphthalen-2-yl)-2-methyl-but-2-enoic acid ethyl ester and 2-Methyl-4-(2,3,4,5-tetramethoxy-6-methyl-phenyl)-but-2-enoic acid ethyl ester which effectuates regio, stereo-specificity and reduces the complexity of building up the final product with higher yields and evading column chromatography. A new concept of "Inhibition of resonance delocalization" (IRD) was used utilizing dithioacetals which undergo umpolung chemistry to couple two prenyl building blocks to construct a higher homologue of the polyprenyl side chain in a stereospecific manner. "Inhibition of resonance delocalization" (IRD) was applied to negate the resonance induced cis-trans isomerization employing dithianeacetal which also facilitates the coupling of two prenyl building blocks to afford a higher prenyl homologue in a stereospecific manner.

Step 1: Synthesis of 2-[3-(1,4-Dimethoxy-3-methyl-naphthalen-2-yl)-1-methyl-propenyl]-[1,3]dithiane Our synthetic preparation started with reduction of menadione to 2-Methyl-naphthalene-1,4-diol, eventually to be converted to 1,4-Dimethoxy-2-methyl-naphthalene (Sch.2. II) before subjecting it to formylation to provide 1,4-Dimethoxy-3-methyl-naphthalene-2-carbaldehyde (Sch.2. III). Homologation of this aldehyde was accomplished by two methods. The first method utilizes the formation of methoxy alkene (under Wittig condition) which under mild acidic condition deliver (1,4-Dimethoxy-3-methyl-naphthalen-2-yl)-acetaldehyde (Sch.2. IV). In an alternative pathway [16] aldehyde (Sch.2. III) was first treated with the ylide, obtained by treating trimethylsulfonium methyl sulfate with alkali, to provide aromatic oxirane which undergoes thermal isomerization to produce (1,4-Dimethoxy-3-methyl-naphthalen-2-yl)-acetaldehyde (Sch.2. IV) (Scheme 1).

One of the salient features of this current invention is to provide 2-[3-(1,4-Dimethoxy-3-methyl-naphthalen-2-yl)-1-methyl-propenyl]-[1,3]dithiane (Sch.2. VIIa), a novel compound, in absolute trans geometry. For the preparation of this compound (Sch.2. Va), Horner-Wadsworth-Emmons (HWE) olefination of the aldehyde (Sch.2. IV) was carried out to form 4-(1,4-Dimethoxy-3-methyl-naphthalen-2-yl)-2-methyl-but-2-enoic acid propyl ester, a β,γ-unsaturated ester, in a stereospecific manner.

Scheme 2. Synthesis of 2-[3-(1,4-Dimethoxy-3-methyl-naphthalen-2-yl)-1-methyl-propenyl]-[1,3]dithiane. This is an important synthon for ensuring the α-double bond stereospecificity in the synthesis of vitamin and its analogues.

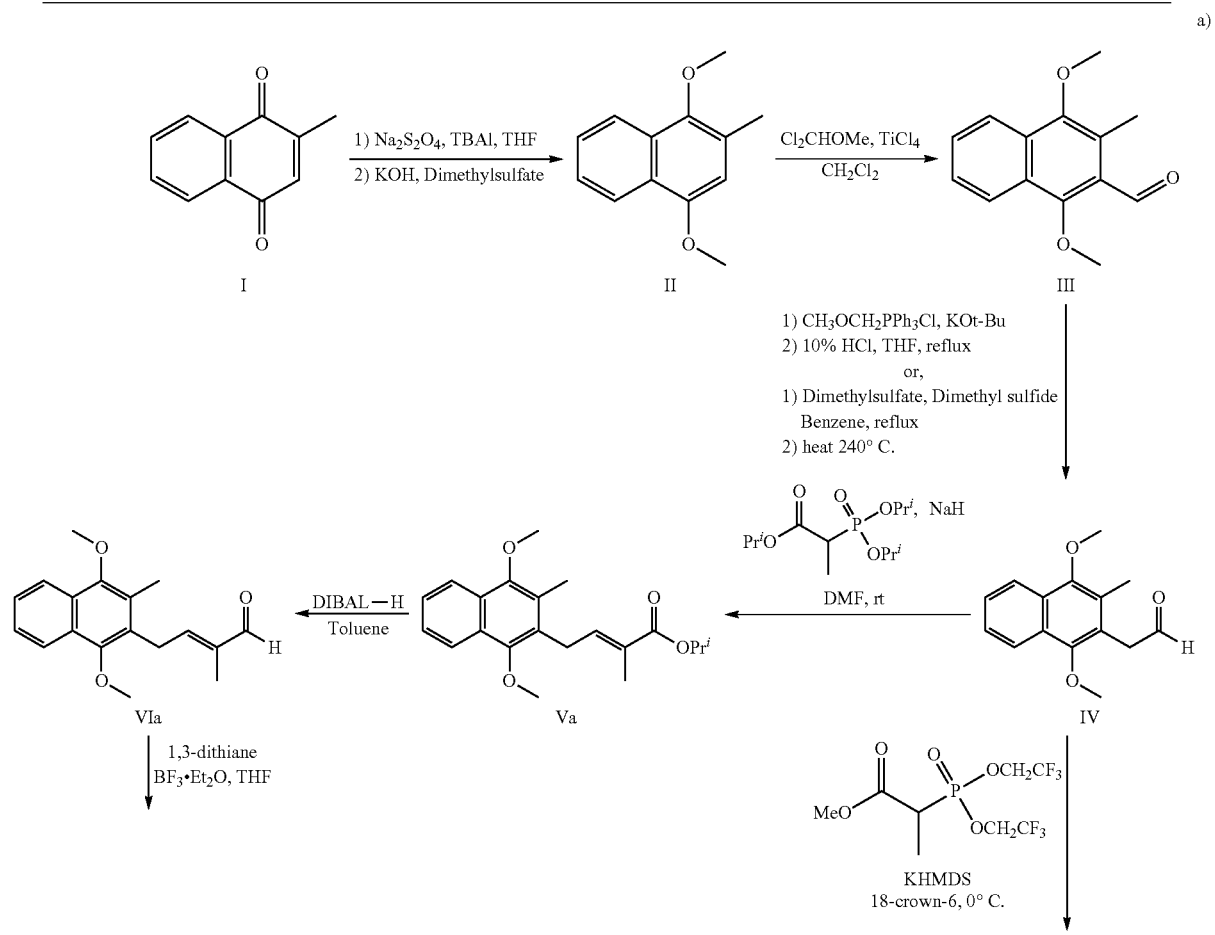

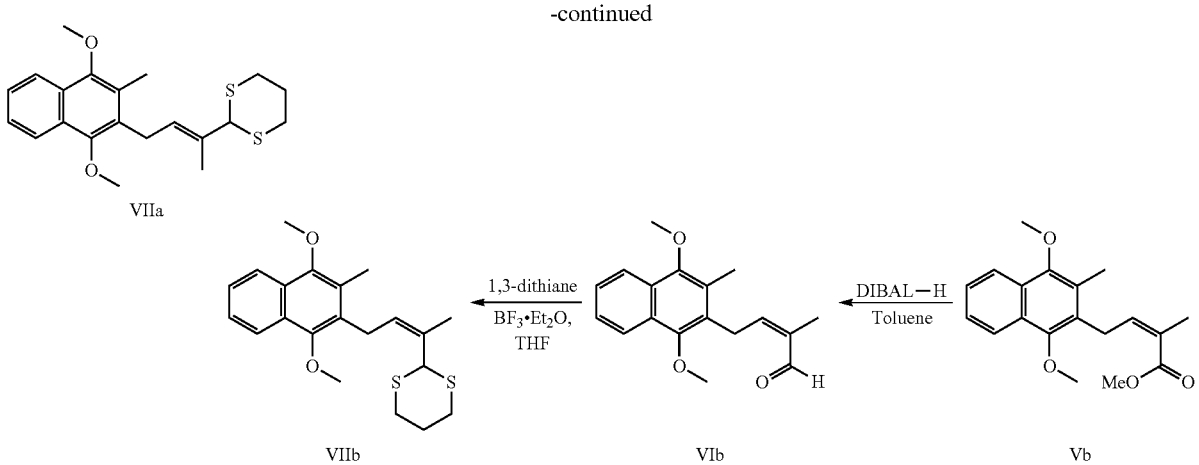

Diisopropylaluminum hydride (DIBAL-H) mediated reduction of ester (Sch.2. Va) provided an aldehyde (Sch.2. VIa) which was converted to a dithiane acetal (Sch.2. VIIa). Employing the Still-Gennari protocol, aldehyde (Sch.2. VIb) can be converted into 2-[3-(1,4-Dimethoxy-3-methyl-naphthalen-2-yl)-1-methyl-propenyl]-[1,3]dithiane (Sch.2. VIIb) stereoselectively.[17, 18, 19, 20]

Step 2: Synthesis of Hexaprenylbromide

The compound of formula (Sch.2. VIIa) is very important as it can provide vitamin K2-4 and, when naphthalene ring is replaced by benzene ring, CoQ10, by using commercially available natural farnesyl and solanesyl derivative respectively. However, a stereospecific synthesis of hexaprenyl bromide is required to complete the synthesis of vitamin K2-7. The synthetic process to combine two prenyl building blocks stereospecifically to yield a higher homologue is mandatory, in order to achieve the all-trans vitamin K and CoQ series. We have made a novel use of 1,3-dithiane related umpolung chemistry which was introduced by Corey and Seebach [21]. Application of dithiane in combining two prenyl building blocks is a very useful in achieving stereoselectivity.

A side chain of hexaprenyl subunit was prepared using commerically available farnesol. Farnesol was at first protected with an acetyl group to generate the compound of formula (Sch.3. II) which was subjected to a $SeO_2$ mediated allylic oxidation leading to the compound of formula (Sch.3. III) along with the corresponding aldehyde. This crude product was treated with sodiumborohydride to afford the compound of formula (Sch.3. III) as a single product. The terminal hydroxyl group of the compound of formula (Sch.3. III) was subsequently converted into its corresponding bromide to facilitate the synthesis of the compound of formula Sch.3. IV) (Scheme 2).

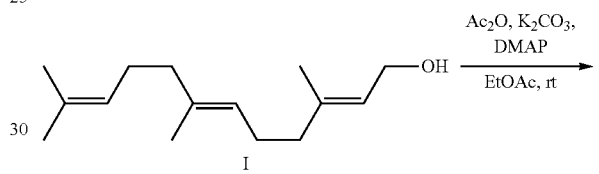

Scheme 3: Synthesis of Acetic acid 12-bromo-3,7,11-trimethyl-dodeca-2,6,10-trienyl ester, an important synthon for the formation of hexaprenol.

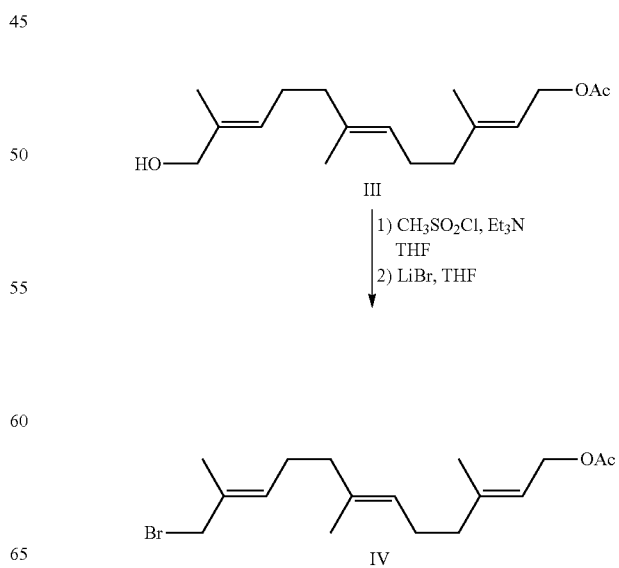

Scheme 4: Final synthesis of hexaprenyl bromide.

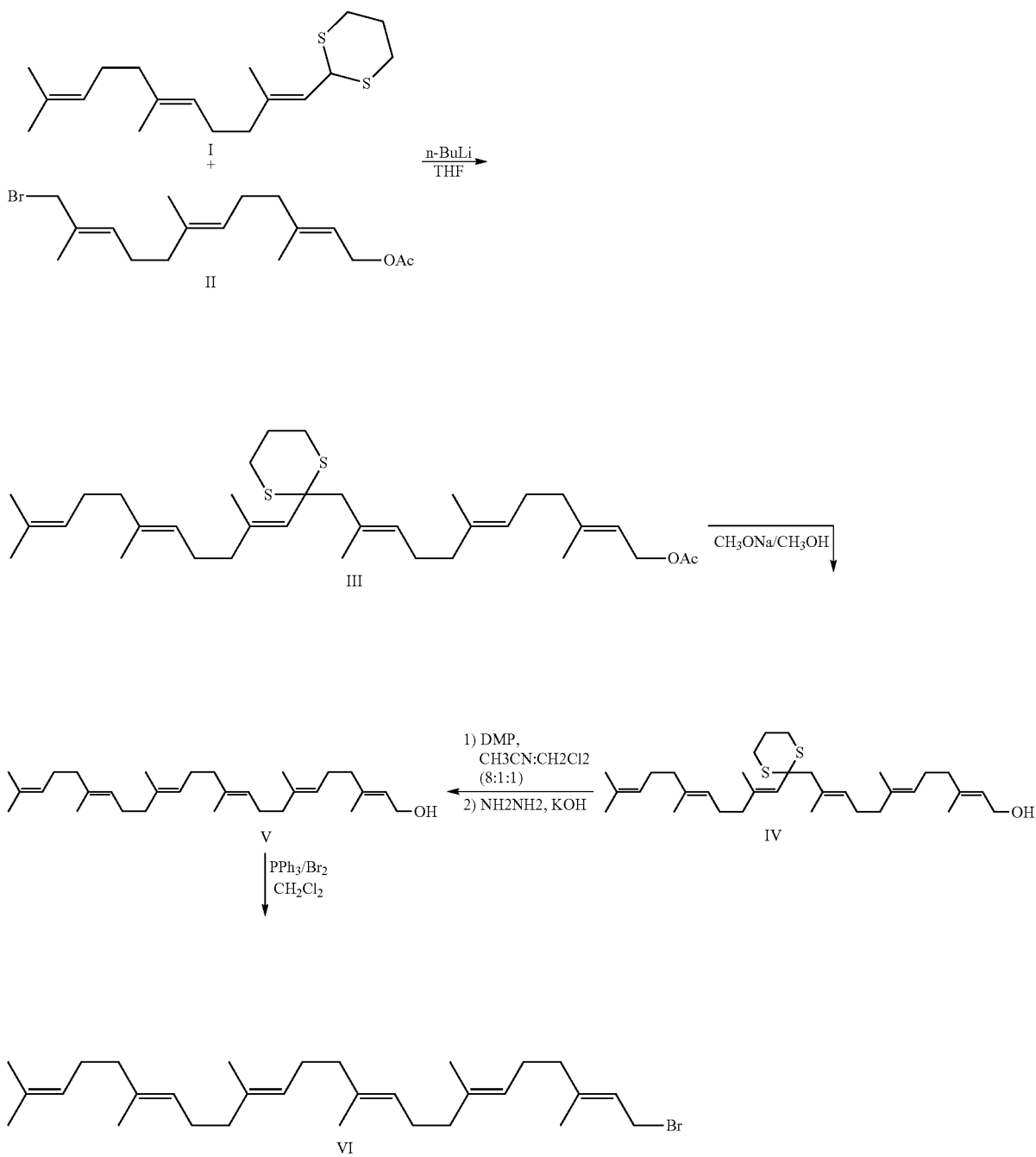

For the synthesis of hexaprenyl bromide (Sch.4. VI), the farnesol dithiane derivative (Sch.4. I) was synthesized by protecting farnesal, obtained by the oxidation of farnesol. The lithiated dithiane moiety, created by treating the compound of formula (Sch.4. I) with n-BuLi, was reacted with the bromo derivative of farnesyl acetate (Sch.4. II) to deliver diprenylated dithiane (Sch.4. III). Wolf-Kishner reduction of the ketone, generated by deprotection of dithiane under a mild condition by applying DMP (Dess-Martin Periodinane), produced hexaprenol (Sch.4. V) in very high yield which was subsequently converted into the hexaprenyl bromide (Sch.4. VI) (Scheme 4).

Step 3: Stereospecific Synthesis of all Trans Vitamin K2-7

Having the compounds (Sch.5. I) and (Sch.5. II) in hand, the process of coupling these two fragments resumed with formation of the compound of formula (Sch.5. III), which undergoes dithiane deprotection to yield the compound (Sch.5. IV). Finally, an oxidative demethylation was performed using ceric ammonium nitrate to provide vitamin K2-7 (Scheme 5).

Scheme 5: Stereospecific synthesis of vitamin K2-7.

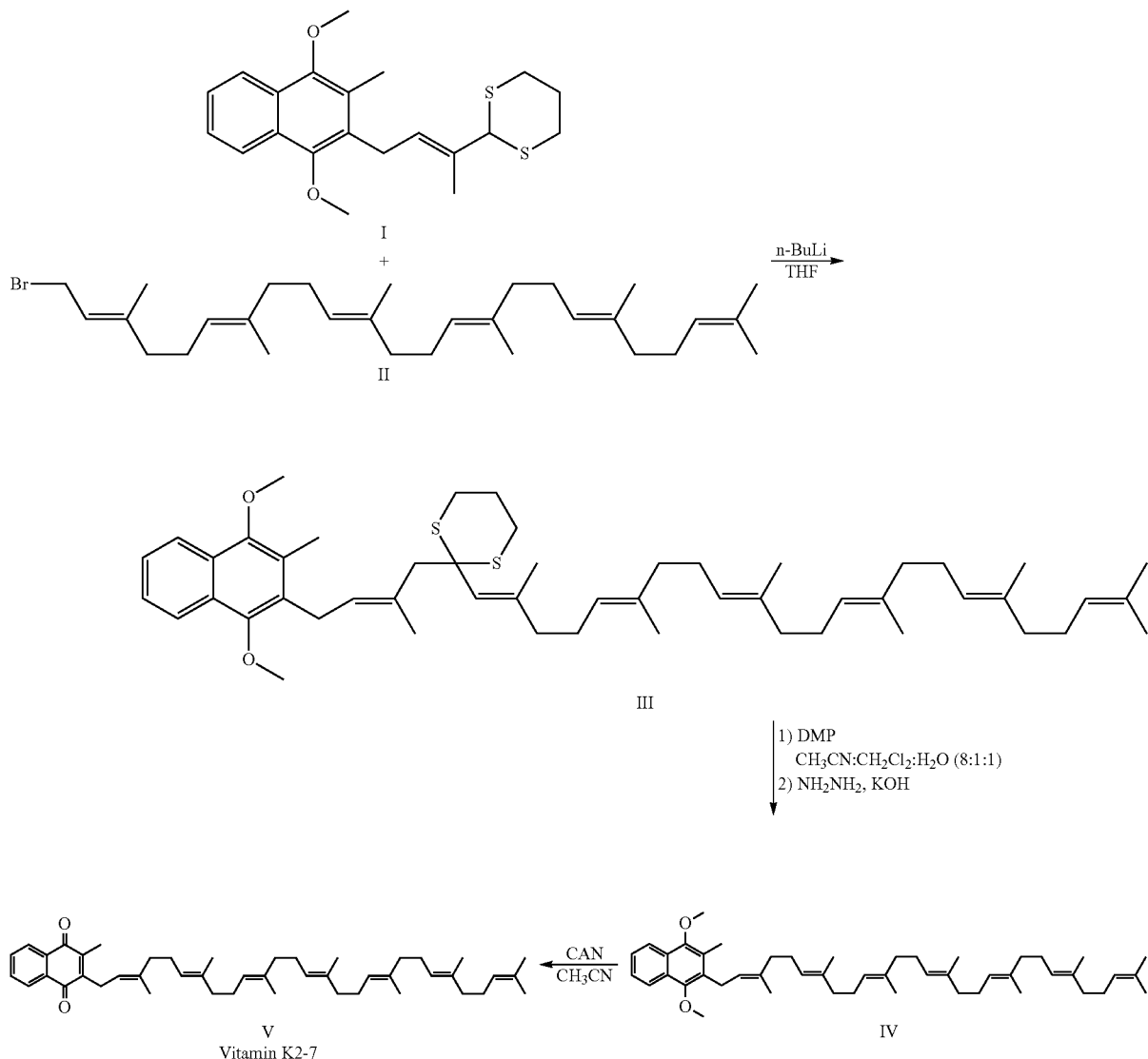

The present inventors have devised a synthetic strategy which facilitates not only the synthesis of trans but when required cis isomer of vitamin K and ubiquinone. There are no earlier reports of such a synthetic scheme which provides for the synthesis of pure all-cis or all-trans isomers of vitamins. This synthetic scheme is a methodology for the preparation of a series of novel polyprenylated quinone derivatives and is not limited to Vitamin K1, the Vitamin K2 series and the CoQ series.

Stereospecific Synthesis of all Trans Vitamin K2-4

Commercially available trans-farnesol was converted into farnesyl bromide (Sch.6. II) before reacting it with the lithiated farnesyl dithiane derivative (Sch.6. III) to afford diprenylated dithiane (Sch.6. III). Deprotection of dithiane followed by oxidative demethylation was carried out in a similar fashion, as explained above to obtain vitamin K2-4.

Scheme 6: Stereospecific synthesis of vitamin K2-4.

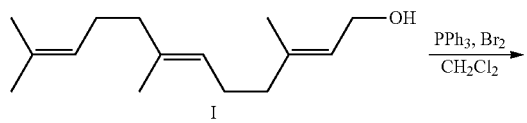

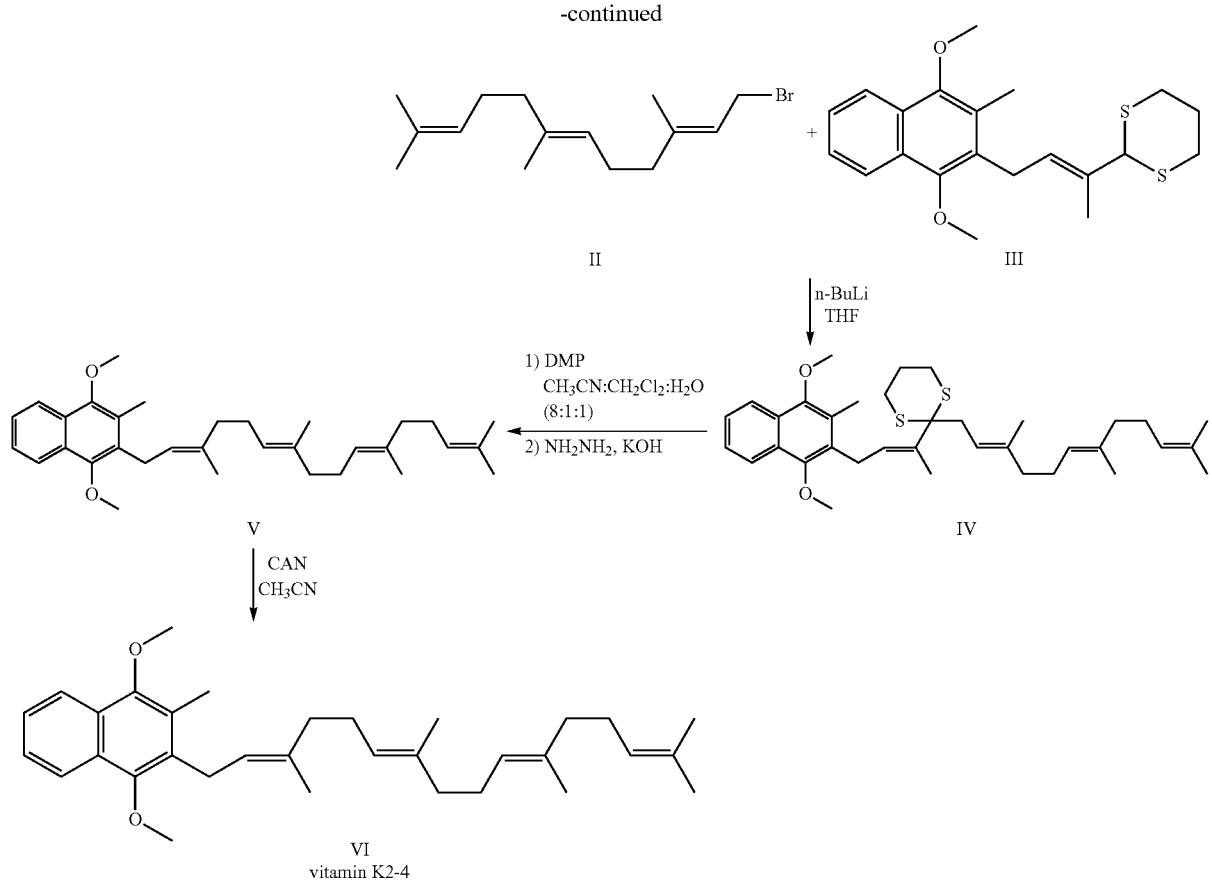

Stereospecific Synthesis of Trans-Phylloquinone

For the synthesis of phylloquinone, an asymmetric hydrogenation of all trans-farnesol was performed using Iridium catalyst to provide the 3R,7R isomer of hexahydrofarnesol (Sch.6. II) which was later converted into the bromide (Sch.7. III) [22]. A lithium salt of the compound (Sch.7. IV) was generated by treating it with n-BuLi and was then treated with compound (Sch.7. III) to furnish coupled product (Sch.7. V). Dithiane deprotection of this coupled product followed by oxidative demethylation paved the path for the synthesis of phylloquinone.

Scheme 7: Stereospecific synthesis of vitamin K-1.

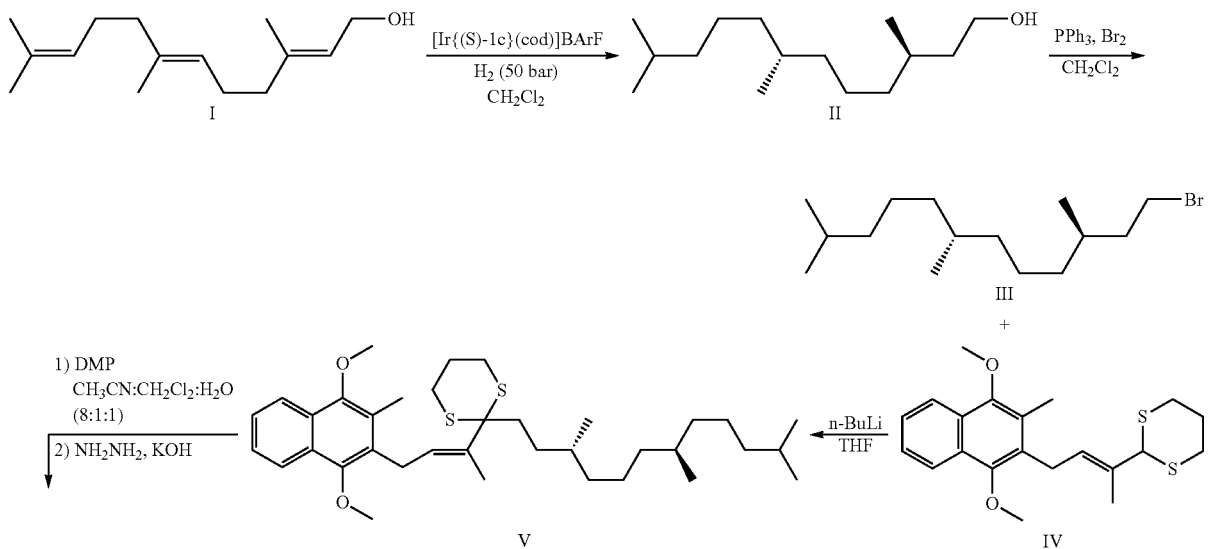

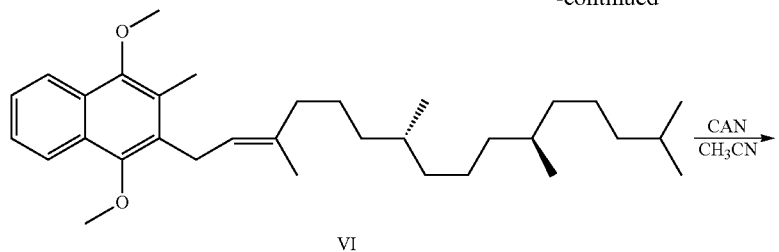

VI

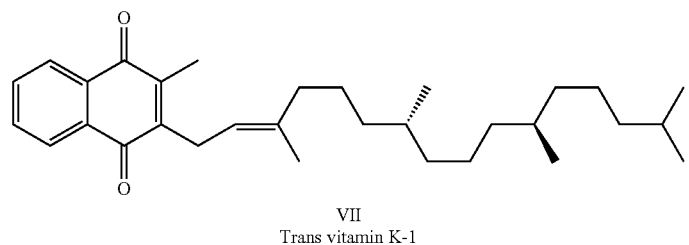

VII
Trans vitamin K-1

Stereospecific Synthesis of all Trans Ubiquinone 1,2,3,4-tetramethoxy-5-methyl-benzene (Sch.8. I), synthesized from p-cresol, was considered as the starting material for the synthesis of ubiquinone. Formylation was achieved to yield 2,3,4,5-tetramethoxy-6-methyl-benzaldehyde (Sch.8. II) which undergoes homologation to provide 2,3,4,5-tetramethoxy-6-methyl-phenyl)-acetaldehyde (Sch.8. III). Application of Horner-Wadsworth-Emmons (HWE) olefination on this aldehyde (Sch.8. III) provided 2-Methyl-4-(2,3,4,5-tetramethoxy-6-methyl-phenyl)-but-2-enoic acid propyl ester (Sch.8. IV) with trans-geometry. 2-Methyl-4-(2,3,4,5-tetramethoxy-6-methyl-phenyl)-but-2-enal (Sch.8. V) was generated by subjecting ester (Sch.8. IV) for a DIBAL-H mediated reduction. Synthesis of 2-[1-Methyl-3-(2,3,4,5-tetramethoxy-6-methyl-phenyl)-propenyl]-[1,3]dithiane (Sch.8. VI) was accomplished by treating aldehyde (Sch.8. V) with 1,3-propandithiol. Having monoprenyl group with dithiane intact on the quinone derivative provides us an advantage to use commercially available solanesol for the synthesis of our target molecule.

Commercially available solanesol was converted into its bromide (Sch.8. VII) before reacting it with lithiated compound (Sch.8. VI) to afford dialkylated dithiane derivative (Sch.8. VIII), which on subjection to a DMP-mediated dithiane deproptection followed by Wolf-Kishner reduction yielded compound of formula (Sch.8. V). Ceric-ammonium nitrate was employed for oxidative demethylation to produce all trans-ubiquione.

Scheme 8: Stereospecific synthesis of CoQ-10.

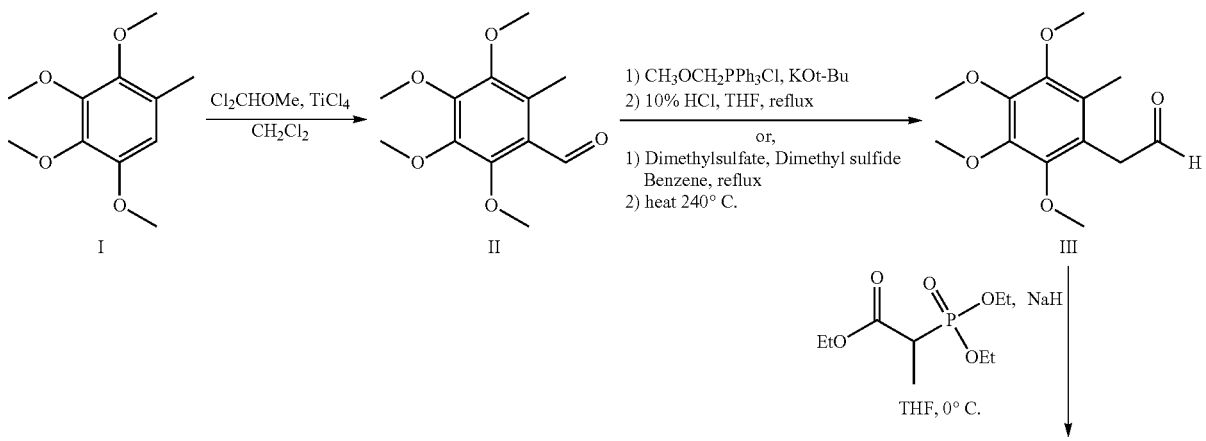

-continued

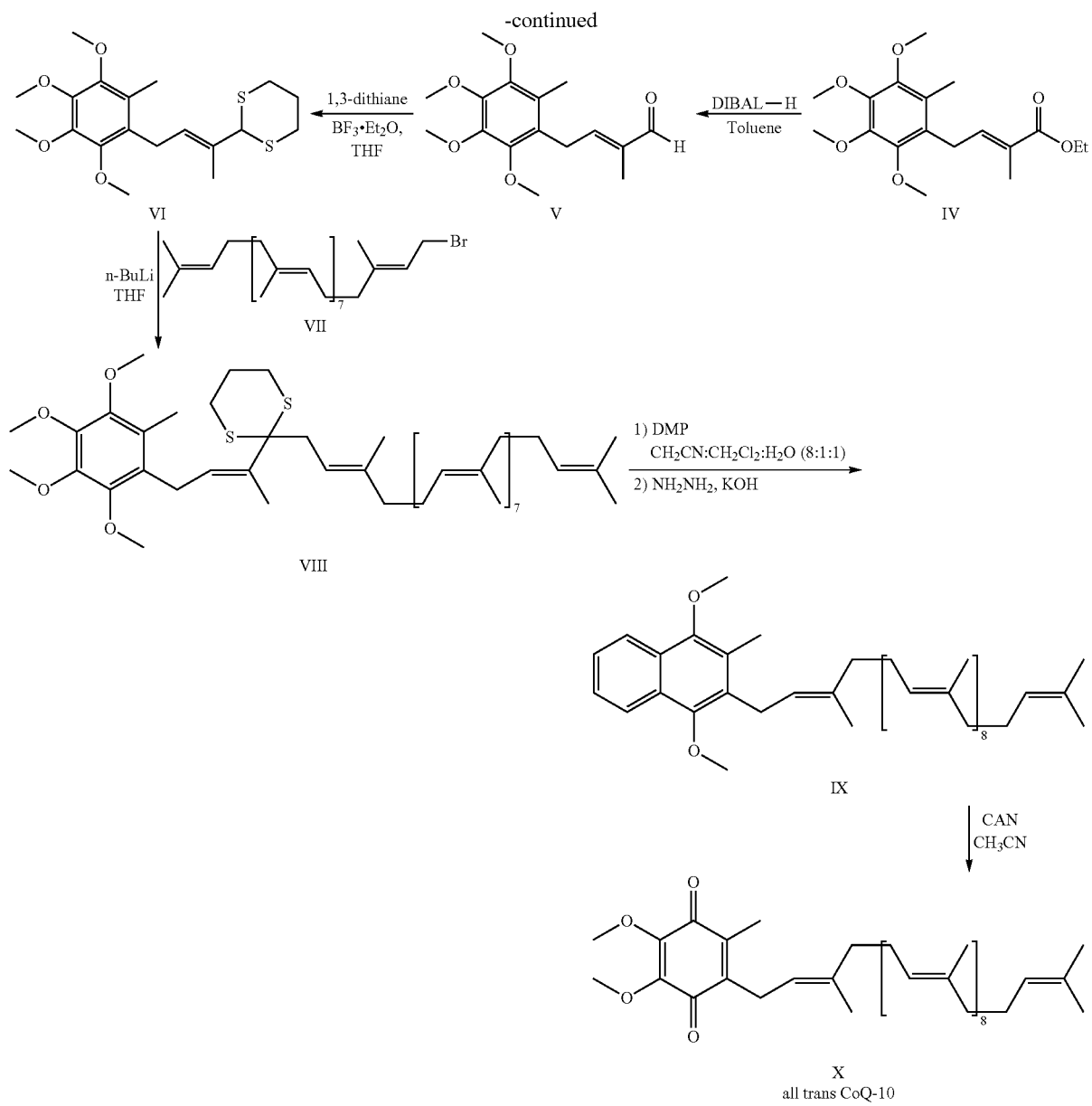

Stereospecific Synthesis of Other Polyprenylated Quinone Derivatives

In addition to vitamin K2-4, K2-7, K-1 and CoQ-10, other polyprenylated all-trans derivatives such as vitamins K2-5, K2-6, K2-8, K2-9, K2-10 can be synthesized based on the synthetic methodology described here. In addition their cis counter parts having a cis bond at the alpha double bond, and, with design, cis at other locations of one or more, can also be prepared by the same scheme of the present scheme as the geometrical purity of this molecule controls the stereo-purity of the α-double bond of vitamin K1, K2 series and ubiquinone series. Further, this starting point reduces the problem to the stereoselective attachment of prenyl side chains.

EXPERIMENTAL
Synthetic Procedures
Examples 1 to 5
Synthesis of β,γ-Unsaturated Ester Synthesis of the stereospecific β,γ-unsaturated ester, a novel compound claimed in this patent, is the starting point The preparation of the β,γ-unsaturated ester was carried out according to the following reaction scheme, consisting of four steps, employing commercially available menadione as the starting material.

Scheme 9: Synthesis of β, γ-unsaturated ester.

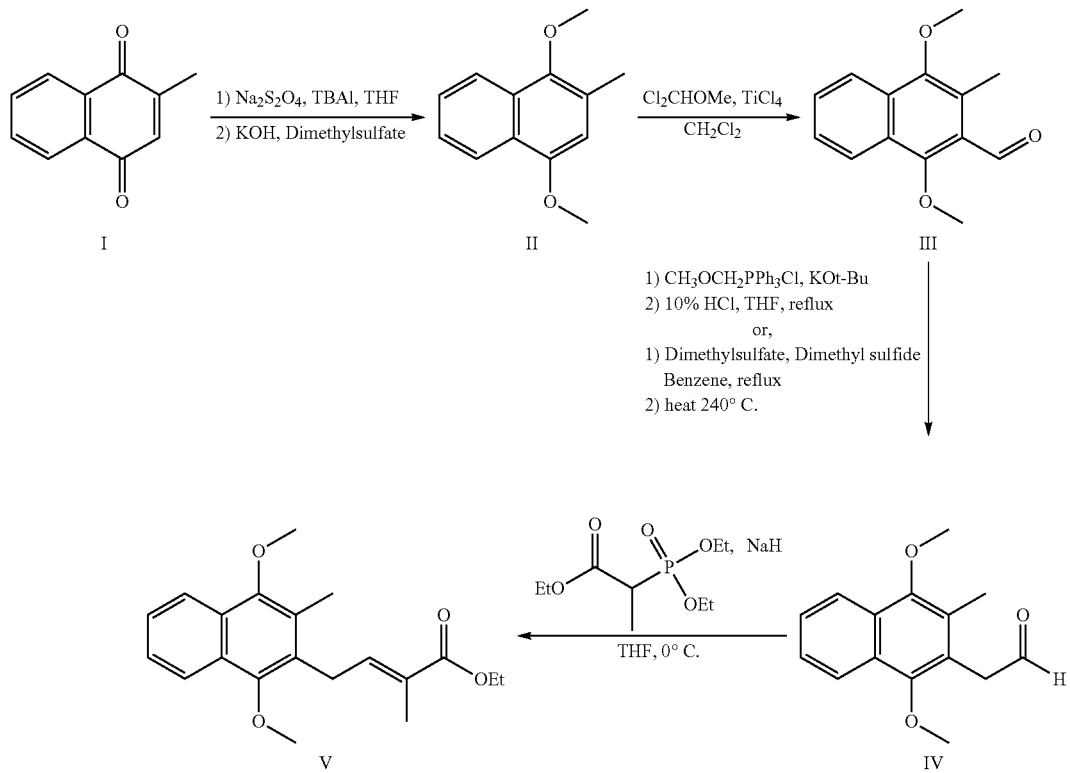

Example 1

Preparation of 2-Methyl-naphthalene-1,4-diol

To a 400 ml solution of

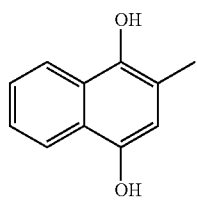

menadione (50 g, 0.29 mol) in EtOAc, was added a solution of sodium dithionite (120 g, 0.69 mol) in 100 ml water under nitrogen atmosphere. The reaction mixture was subjected to vigorous stirring. The discoloration of the organic layer indicated the completion of the reaction which was supported by TLC observation. Then 100 ml of 1M Sodium metabisulfite solution was added. The aqueous layer was separated and extracted with Ethyl acetate (2×50 ml). The combined organic layers were washed with saturated sodium chloride solution and finally dried over MgSO$_4$ before evaporating the solvent in vacuum. A pale purple solid was recovered which was titurated with 300 ml of hexanes and the solid was filtered off to obtain 2-Methyl-naphthalene-1, 4-diol (50 g, 98% yield) which was used for the next reaction without any purification.

Example 2

Synthesis of 1,4-Dimethoxy-2-methyl-naphthalene

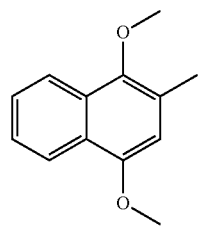

To a 50 ml solution of 2-Methyl-naphthalene-1,4-diol (3.8 g, 0.022 mol) in acetone was sequentially added K$_2$CO$_3$ (15.20 g, 0.11 mol) and dimethylsulfate (10.43 ml, 0.110 mol). The resulting orange colored reaction mixture was refluxed for 6 h at which time TLC indicated the completion of the reaction. The reaction mixture was the filtered and the filtrate was treated with 1N NaOH solution to adjust the pH to 5 or 6. The organic layer was separated and washed with brine before drying over Na$_2$SO$_4$. Solvent was removed under reduced pressure to provide a thick oil (3.7 g, 85%) which eventually solidified at lower temperature. $^1$H NMR (400 MHz, CDCl$_3$): 8.17-8.19 (d, 1H, J=8.24 Hz), 8.00-8.02 (d, 1H, J=8.24 Hz), 7.50-7.41 (t, 1H, J=8.24 Hz), 6.59 (s, 1H), 3.85 (s, 3H), 2.44 (s, 3H), 1.42 (s, 3H).

Example 3

Synthesis of 1,4-Dimethoxy-3-methyl-naphthalene-2-carbaldehyde

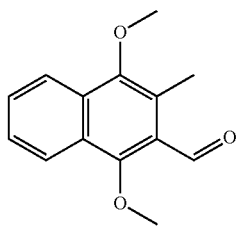 [SMILES: COc1c(C)c(C=O)c(OC)c2ccccc12]

TiCl$_4$ was added, dropwise, to a 30 ml CH$_2$Cl$_2$ solution of dimethoxy naphthalene (5.0 g, 0.024 mol) at −45° C. under nitrogen atmosphere. To this reaction mixture, 1,1-dichloromethoxy methane (2.76 g, 0.024 mol) was added drop wise and the reaction mixture was stirred, for 10 minutes before bringing the bath temperature to 0° C. After stirring the reaction mixture for an additional 2 hours, TLC indicated the consumption of starting material. All the contents of the reaction flask were transferred to a separatory funnel containing 150 ml EtOAc before quenching it with 30 ml of H$_2$O. The organic layer was separated and aqueous layer was further extracted with EtOAc (20 ml). The organic layers were combined and washed with brine solution (30 ml) before drying over MgSO$_4$. The solvent was evaporated under vacuum to provide a thick oil which solidified at lower temperature. The solid was triturated with iso-propanol to afford aldehyde (5.25, 95% yield). $^1$H NMR (400 MHz, CDCl$_3$): 10.68 (s, 1H), 8.14 (d, 1H, J=8.2 Hz) 8.07 (d, 1H, J=8.2 Hz), 7.61-7.60 (t, 1H, J=1.4 Hz), 7.52-7.50 (t, 1H, J=8.2 Hz), 4.02 (s, 3H), 3.82 (s, 3H), 2.60 (s, 3H).

Example 4

Synthesis of (1,4-Dimethoxy-3-methyl-naphthalen-2-yl)-acetaldehyde

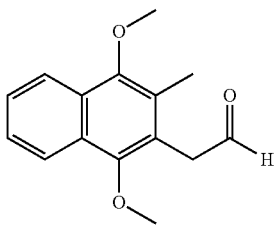 [SMILES: COc1c(C)c(CC=O)c(OC)c2ccccc12]

Potassium tert-butoxide was added to a 25 ml THF solution of methoxymethyltriphenylphosphonium bromide (2.6 g, 0.007 mol) at 0° C. to generate a ylide. After stirring the ylide at this temperature for 30 minutes a solution of 1,4-Dimethoxy-3-methyl-naphthalene-2-carbaldehyde (1.0 g, 0.0043 mol) was added dropwise over 15 min. This orange colored reaction mixture was further stirred for 2 hours at which time the TLC indicated the consumption of the starting material. All the contents of the reaction mixture were transferred to a separatory funnel containing EtOAc (150 ml) and the reaction mixture was quenched by the slow addition of brine. The organic layer was separated, and the aqueous layer was extracted with EtOAc (30 ml). The organic layers were combined and washed with brine before drying over MgSO$_4$. The solvent was removed under vacuum to furnish a yellow liquid. The crude product obtained from the reaction was mixed with THF (30 ml) and 10% aq. HCl (5 ml) and subjected to refluxing. The reaction was found to reach completion in 40 minutes. The THF was removed under vacuum before mixing with EtOAc (100 ml) and the reaction mixture was quenched by addition of saturated NaHCO$_3$. The organic layer was removed under vacuum and the product obtained was found to be solidify at lower temperatures, providing (1,4-Dimethoxy-3-methyl-naphthalen-2-yl)-acetaldehyde as solid. $^1$H NMR (400 MHz, CDCl$_3$): 9.76 (s, 1H), 8.07 (m, 1H) 7.48 (m, 1H), 7.45 (m, 1H), 7.43 (m, 1H), 3.95 (d, 2H, J=1.8 Hz) 3.86 (s, 3H), 3.84 (s, 3H).

Example 5

Synthesis of 4-(1,4-Dimethoxy-3-methyl-naphthalen-2-yl)-2-methyl-but-2-enoic acid ethyl ester

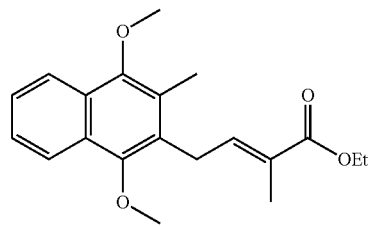 [SMILES: CCOC(=O)/C(C)=C/Cc1c(C)c(OC)c2ccccc2c1OC]

To a 20 ml suspension of NaH (0.73 g, 0.018 mol) in THF under nitrogen atmosphere was added triethyl 2-phosphonopropionate (4.28 g, 0.018 mol) drop wise at 0° C. which was then stirred for 30 minutes before adding (1,4-Dimethoxy-3-methyl-naphthalen-2-yl)-acetaldehyde (3.0 g, 0.012 mol) dissolved in THF (10 ml). Subsequently, this reaction mixture was stirred for 14 hrs at which time TLC indicated the consumption of the starting material. The reaction mixture was quenched by addition of brine and the contents of the reaction flask were transferred to a separatory funnel containing EtOAc (100 ml). The organic layer was washed with water (2×20 ml). The collected aqueous layer was then extracted with EtOAc (30 ml). The organic layers were combined, washed with brine (30 ml) before drying over MgSO$_4$. The solvent was removed under vacuum to obtain a crude ester as a thick oil (3.3 g, 85%) which was subjected to further reduction without any purification.

Examples 6 to 8

Synthesis of aromatic building block 2-[3-(1,4-Dimethoxy-3-methyl-naphthalen-2-yl)-1-methyl-propenyl]-[1,3]dithiane(Ia)

The synthesis of The stereospecific β,γ-unsaturated ester, a novel compound claimed in this patent, serves in the synthesis of another novel compound 2-[3-(1,4-Dimethoxy-3-methyl-naphthalen-2-yl)-1-methyl-propenyl]-[1,3]dithiane (Sch.10. III) which is key to the stereoselective attachment of the prenyl side chains.

Scheme 10: Synthesis of 2-[3-(1,4-Dimethoxy-3-methyl-naphthalen-2-yl)-1-methyl-propenyl]-[1,3]dithiane.

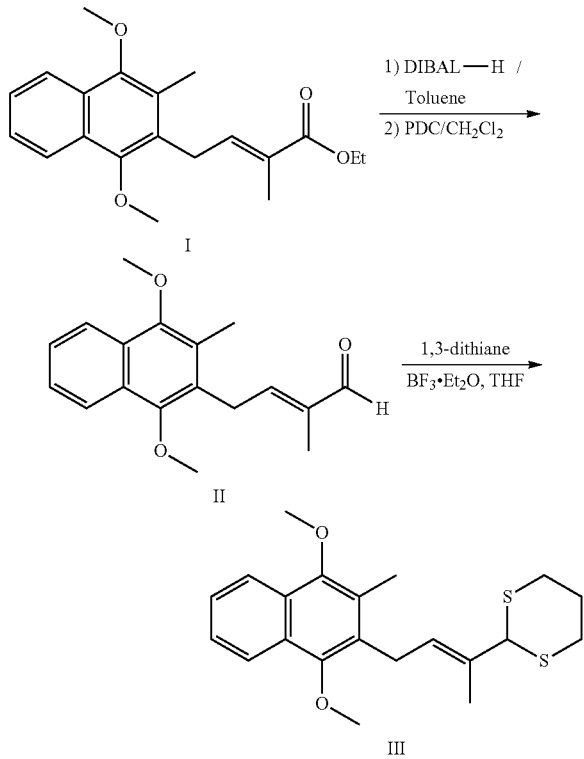

Example 6

Synthesis of 4-(1,4-Dimethoxy-3-methyl-naphthalen-2-yl)-2-methyl-but-2-en-1-ol

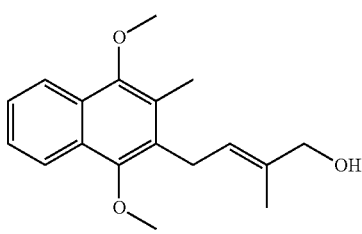 [SMILES: COc1c(C)c(C/C=C(\C)CO)c(OC)c2ccccc12]

To a 100 ml solution of crude 4-(1,4-Dimethoxy-3-methyl-naphthalen-2-yl)-2-methyl-but-2-enoic acid ethyl ester (3.3 g, 0.010 mol) in THF under a nitrogen atmosphere, was added DIBAL-H (15 ml, 0.015 mol) dropwise. This reaction mixture was stirred for 6 hours at which time all the starting material was consumed as indicated by TLC. This reaction mixture was then quenched by adding 1N NaOH drop wise until the effervescence ceased. It was then allowed to stir for another hour before filtering through a pad of celite. The filtrate thus obtained was transferred to a separatory funnel containing EtOAc (100 ml). The organic layer was separated, washed with brine and finally dried over $MgSO_4$. The solvent was removed under vacuum to obtain 4-(1,4-Dimethoxy-3-methyl-naphthalen-2-yl)-2-methyl-but-2-en-1-ol (2.6 g, 91%) as colorless oil. $^1$H NMR (400 MHz, $CDCl_3$): 8.03 (m, 2H, J=8.2 Hz), 7.46 (m, 2H, J=3.8 Hz), 5.40 (t, 1H, J=1.6 Hz), 4.21-4.18 (t, 1H, J=6.4 Hz), 4.00 (s, 2H), 3.87 (s, 3H), 3.84 (s, 3H), 3.59-3.58 (d, 2H, J=5.96 Hz), 2.36 (s, 3H), 1.87 (s, 3H).

Example 7

Synthesis of 4-(1,4-Dimethoxy-3-methyl-naphthalen-2-yl)-2-methyl-but-2-enal

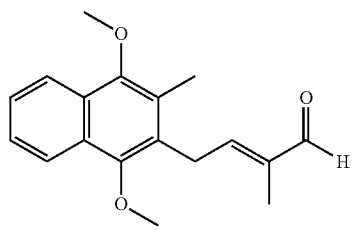 [SMILES: COc1c(C)c(C/C=C(\C)C=O)c(OC)c2ccccc12]

To a solution of 4-(1,4-Dimethoxy-3-methyl-naphthalen-2-yl)-2-methyl-but-2-en-1-ol (2.6 g, 0.009 mol) in DMF (20 ml) under a nitrogen atmosphere, was added pyridium dichromate (4.10 g, 0.010 mol) in installments. This reaction was stirred at room temperature until the consumption of starting material. This reaction mixture was then passed through a pad of silica and eluted with 10% EtOAc/hexanes to obtain the corresponding aldehyde as a yellow oil (2.2 g, 88% yield). This crude aldehyde was subjected for protection as dithianeacetal without any purification. (??Sentence unclear)

Example 8

Synthesis of 2-[3-(1,4-Dimethoxy-3-methyl-naphthalen-2-yl)-1-methyl-propenyl]-[1,3]dithiane

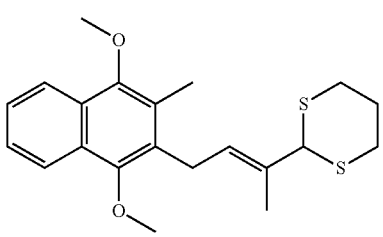 [SMILES: COc1c(C)c(C/C=C(\C)C2SCCCS2)c(OC)c2ccccc12]

To a solution of 4-(1,4-Dimethoxy-3-methyl-naphthalen-2-yl)-2-methyl-but-2-enal (2.2, 0.0077 mol) and 1,3-propanedithiol (1.00 g, 0.0092 mol) in $CHCl_3$ (25 mL) was added iodine (0.23 g, 0.00092 mol), and the resulting mixture was allowed to stir at room temperature for 6 hrs at which time TLC ensured the completion of the reaction. The reaction was quenched by adding saturated $Na_2S_2O_3$ and 1N NaOH respectively. Then $CHCl_3$ (80 ml) was added to the resulting reaction mixture. The organic layer was separated and washed with $H_2O$. The organic layer was dried over $MgSO_4$ before washing with brine (10 ml) and was finally removed under vacuum to supply 2-[3-(1,4-Dimethoxy-3-methyl-naphthalen-2-yl)-1-methyl-propenyl]-[1,3]dithiane (2.7, 94%).

Examples 9 to 17

Synthesis of Hexaprenyl Bromide

Having prepared the dithianeacetal derivative of the quinone moiety, the synthesis of a polyprenyl side chain without loss of stereochemistry, of the required number of prenyl units, is second most important task in the preparation of native vitamin K2-7. On the other hand, the innovative approach of this patent permits the direct use of commercially available all-trans natural side chains, farnesyl and solanesyl, in the preparation of native all-trans vitamin K2-4 and coenzyme Q10.

After conducting a retrosynthetic analysis of hexaprenyl bromide (Sch.11. I), we envisaged the farnesyldithiane (Sch.11. II) derivative and the bromo farnesyl acetate (Sch.11. III) as important synthons required to construct a C—C bond to provide our target compound.

Scheme 11: Retrosynthetic analysis of hexaprenyl bromide

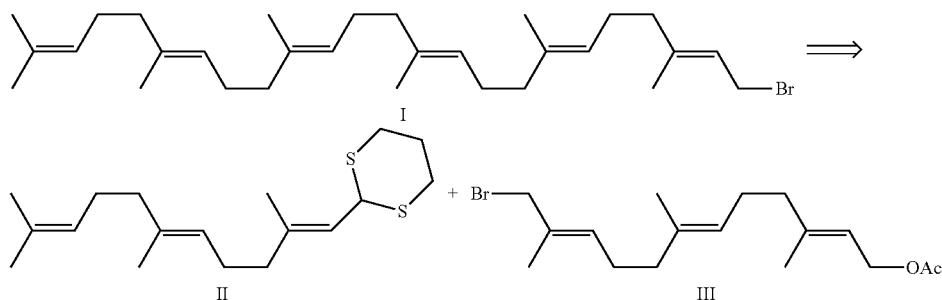

The use of farnesyldithioacetal (Sch.11. II), in the synthesis of the hexaprenyl bromide, as explained earlier, gets around delocalization of electrons on the π-electron cloud of double bond and grants attachment of two polyprenyl chains without loss of stereoselectivity.

Scheme 12. Synthesis of farnesyldithiane derivative.

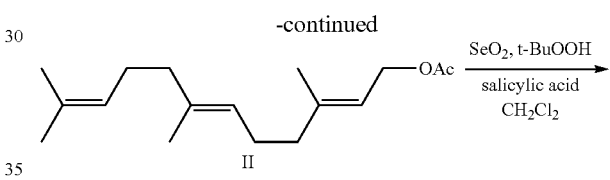

After the formation of 2-(2,6,10-Trimethyl-undeca-1,5,9-trienyl)-[1,3]dithiane (Sch.12. III), synthesis of the other building block was pursued. Commercially available all trans-farnesol was converted to farnesyl acetate (Sch.12. II) which undergoes allylic oxidation to deliver hydroxyl farnesylacetate (Sch.12. III). Synthesis of the acetic acid 12-bromo-3,7,11-trimethyl-dodeca-2,6,10-trienyl ester (Sch.12. IV) was completed by converting the terminal hydroxyl group into its bromide.

Scheme 13. Synthesis of Acetic acid 12-bromo-3,7,11-trimethyl-dodeca-2,6,10-trienyl ester.

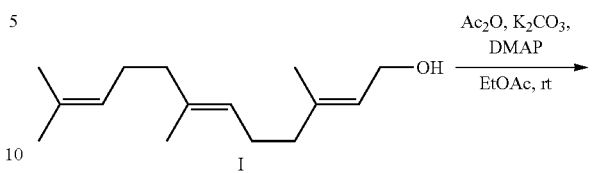

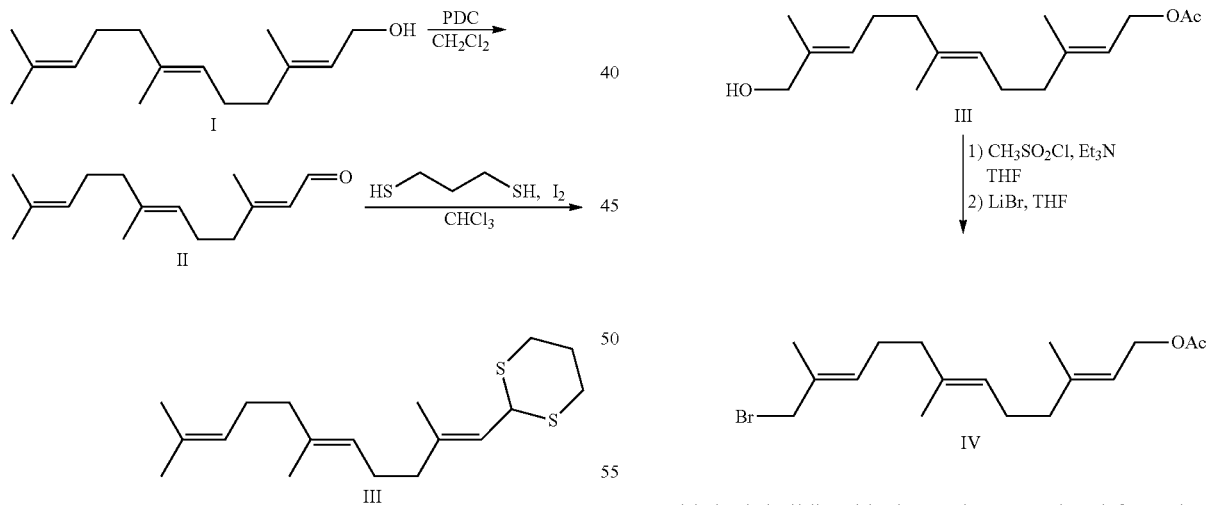

With both building blocks ready, C—C bond formation was accomplished by treating the bromo farnesylacetate (Sch.13. II) with the lithium salt of the farnesyldithiane derivative (Sch.13. I), obtained by treating the compound (Sch.13. I), with n-BuLi. The coupled product (Sch.13. III) was deacylated under mild basic conditions to furnish (Sch.13. IV). Removal of dithaine was engineered in two steps; first it was converted into the ketone, by applying the Dess-Martin periodinane (DMP) reagent, and was further reduced into an alkyl group under the Wolf-Kishner protocol to provide the hexaprenol (Sch.13. V).

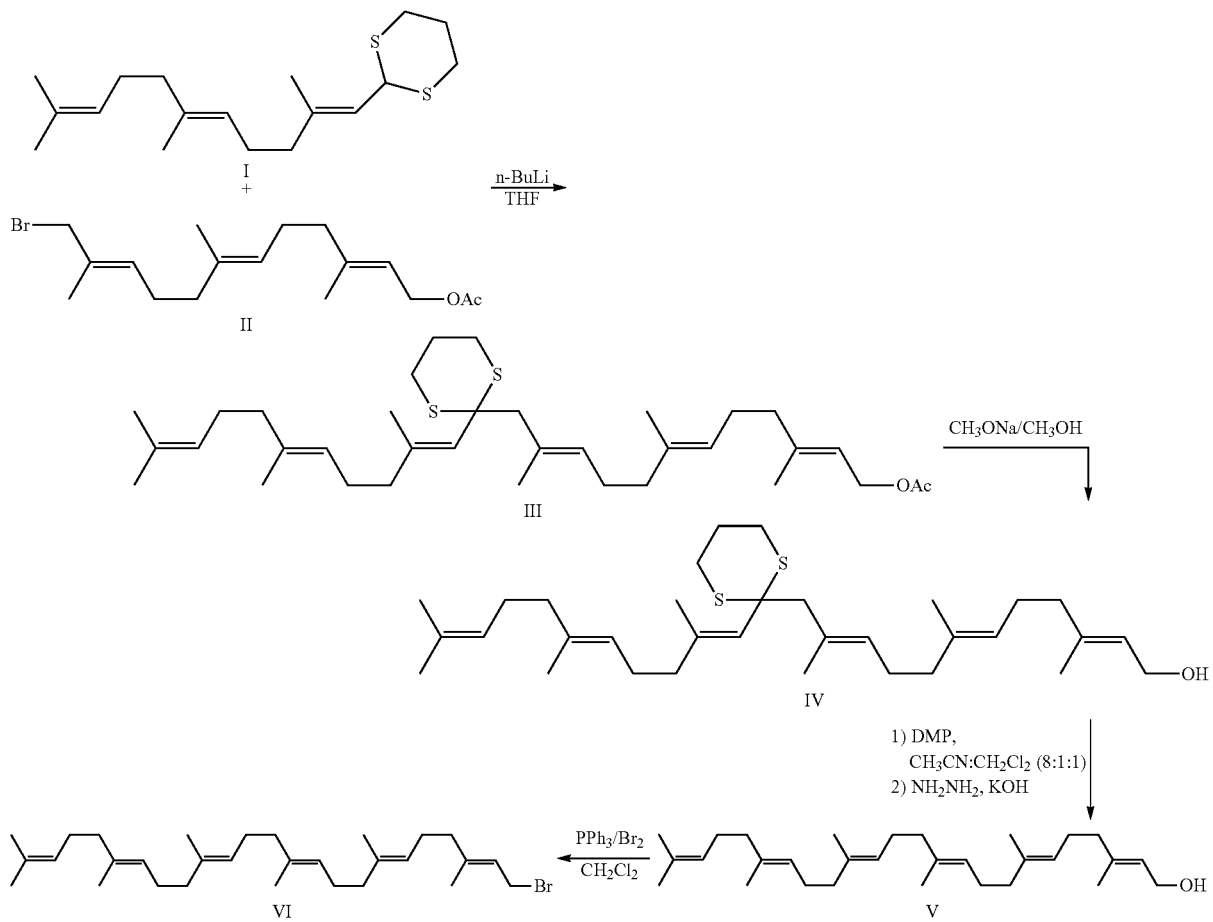

Scheme 14. Synthesis of hexaprenyl bromide

Example 9

Synthesis of 3,7,11-Trimethyl-dodeca-2,6,10-trienal (Farnesal)

To a solution of farnesol (10 g, 0.045) in CH$_2$Cl$_2$ (150 ml) under nitrogen atmosphere was added pyridinium dichromate (25 g, 0.067 mol) in installments. This reaction was found to be completed in 1 hour. All the contents of the reaction mixture was passed through a pad of celite, filterate obtained was removed under vacuum to yield farnesal (9.2 g, 93%) as a colorless liquid. $^1$H NMR (400 MHz, CDCl$_3$): 9.98 (d, 1H, J=8.24 Hz), 5.87 (d, 1H, J=9.16 Hz), 5.06 (m, 2H), 2.24 (m, 4H), 2.15 (s, 3H), 2.04 (m, 4H), 1.95 (s, 3H), 1.60 (s, 3H), 1.40 (s, 3H).

Example 10

Synthesis of 2-(2,6,10-Trimethyl-undeca-1,5,9-trienyl)-[1,3]dithiane

To a solution of Farnesal (5.5 g, 0.025 mol) and 1,3-propanedithiol (3.13 g, 0.029 mol) in CHCl$_3$ (45 mL) was added iodine (0.5 g, 0.002 mol), and the resulting mixture was allowed to stir at room temperature for 6 hrs at which time TLC ensured the completion of the reaction. The reaction was quenched by adding saturated Na$_2$S$_2$O$_3$ and 1N NaOH respectively. Then CHCl$_3$ was added to the resulting reaction mixture. The organic layer was separated and was washed with H$_2$O. The organic layer was dried over MgSO$_4$ before washing with brine (10 ml) and was finally removed under vacuum to produce 2-(2,6,10-Trimethyl-undeca-1,5,9-trienyl)-[1,3]dithiane (6.8, 87%).

Example 11

Synthesis of Acetic acid 3,7,11-trimethyl-dodeca-2,6,10-trienyl ester, or Farnesyl acetate

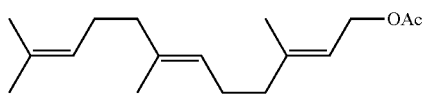

To a solution of farnesol (100 g, 0.45 mol), potassium carbonate (90 g, 0.65 mol) and 4-dimethylamino pyridine (0.5 g) in EtOAc (300 ml) at 0° C., acetic anhydride (66.5 g, 0.65 mol) was added dropwise. The reaction was finished in 2 hrs. All the contents of the reaction flask were transferred to a conical flask containing EtOAc (600 ml) and treated with the dropwise addition of a saturated NaHCO$_3$ solution. After neutralization, the organic layer was separated and washed with water (2×80 ml), brine (80 ml), and dried over MgSO$_4$ and then removed under vacuum to yield the farnesyl acetate (108 g, 92%). $^1$H NMR (400 MHz, CDCl$_3$): 5.34 (t, 1H, J=6.04 Hz), 5.07 (m, 2H), 4.57 (d, 2H, J=6.84 Hz), 2.10-2.05 (m, 11H), 1.97-1.95 (m, 2H), 1.68-1.66 (m, 6H), 1.58 (s, 6H).

Example 12

Synthesis of Acetic acid 12-hydroxy-3,7,11-trimethyl-dodeca-2,6,10-trienyl ester

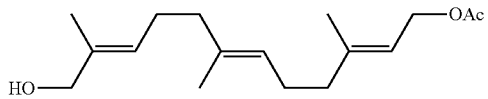

To a solution of SeO$_2$ (4.52 g, 0.040 mol), salicylic acid (5.63 g, 0.040 mol) in CH$_2$Cl$_2$ (300 ml) was added tert-butylhydrogen peroxide (183 g, 1.63 mol), and the reaction mixture stirred at room temperature until homogeneity. This mixture was brought to 0° C. before adding the farnesyl acetate (108 g, 0.40 mol) dissolved in CH$_2$Cl$_2$ (100 ml) to it. The reaction mixture was stirred for 14 hours until completion. The CH$_2$Cl$_2$ was removed under vacuum and the crude product diluted with toluene (400 ml) before neutralizing it very carefully with saturated NaHCO$_3$ solution. The toluene solution was then separated, washed with brine (2×50 ml), dried over MgSO$_4$, and finally removed under vacuum to provide a mixture of the desired alcohol and aldehyde. The crude product was then diluted in methanol and treated with NaBH$_4$ (8.32 g, 0.22 mol) in installments. The reaction was completed in 2 hrs and was neutralized by drop wise addition of 1M HCl. All the contents of the reaction flask were transferred to a separatory funnel containing EtOAc (500 ml). The organic layer was separated, washed with brine and finally dried over MgSO$_4$. The solvent was removed under vacuum to furnish the desired alcohol (65 g, 59%). $^1$H NMR (400 MHz, CDCl$_3$): 5.35-5.29 (m, 2H), 5.07-5.06 (t, 1H, J=6.7 Hz), 4.56 (d, 2H, J=7.32 Hz), 3.96 (s, 2H), 2.04-1.96 (m, 10H), 1.69-1.63 (m, 10H).

Example 13

Synthesis of Acetic acid 12-bromo-3,7,11-trimethyl-dodeca-2,6,10-trienyl ester

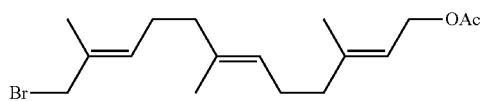 [SMILES: CC(=O)OC/C=C(\C)CC/C=C(\C)CC/C=C(\C)CBr]

To a 40 ml THF solution of the alcohol (Sch.13. III) (4.48 g, 0.016 mol) at −40° C., was added methanesulfonyl chloride (2.38 g, 0.020 mol) followed by the drop wise addition of triethyl amine (3.23 g, 0.011 mol). A white solid compound starts to appear after addition of triethylamine. The reaction mixture was further stirred for 45 minutes at −45° C. and then brought to 0° C. before adding a solution of lithium bromide (1.58 g, 0.018 mol) dissolved in THF (30 ml). This was then for 2 hours. After ensuring the consumption of starting material, the reaction was quenched by drop wise addition of NaHCO3. The THF was then removed under vacuum and the crude product diluted with EtOAc (100 ml) and washed with water (3×30 ml). The aqueous layer obtained was further extracted with EtOAc (2×20 ml). The organic layers were combined, washed with brine (30 ml) and then dried over MgSO$_4$ before removing the solvent under vacuum to yield the acetic acid 12-bromo-3,7,11-trimethyl-dodeca-2,6,10-trienyl ester (Sch.13. IV), which was used immediately without any purification, because of its instability. $^1$H NMR (400 MHz, CDCl$_3$): 5.57-5.55 (t, 1H, J=7.32 Hz), 5.34-5.30 (t, 1H, J=5.9 Hz), 5.09-5.06 (t, 1H, J=5.52 Hz), 4.57-4.56 (d, 2H, J=7.36 Hz), 3.99-3.98 (s, 2H), 2.25-2.03 (m, 10H), 1.76-1.66 (m, 10H).

Example 14

Synthesis of Acetic acid 3,7,11-trimethyl-12-[2-(2,6,10-trimethyl-undeca-1,5,9-trienyl)-[1,3]dithian-2-yl]-dodeca-2,6,10-trienyl ester

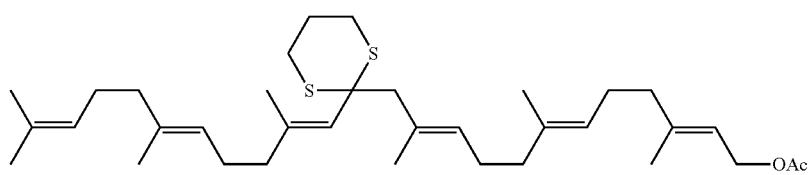 [SMILES: CC(=O)OC/C=C(\C)CC/C=C(\C)CC/C=C(\C)CC1(/C=C(\C)CC/C=C(\C)CCC=C(C)C)SCCCS1]

To a solution of the compound (Sch.14. I) (1.8 g, 0.006 mol) in THF, under a nitrogen atmosphere, was added n-BuLi (8.7 ml, 0.0057 mol) dropwise at −78° C. and then stirred for 40 minutes before adding a solution of the compound (Sch.14. II) (2.38 g, 0.007 mol) in THF. This reaction mixture was stirred until the consumption of the limiting reagent, after which it was quenched by cold saturated NH$_4$Cl solution. All the contents of reaction mixture were transferred to a separatory funnel containing EtOAc (100 ml). Organic layer was separated while aqueous layer was extracted with EtOAc (2×25 ml). The organic layers were collected and washed with brine, dried over MgSO$_4$ before removing under vacuum to obtain the crude compound (2.8 g, 85% yield) as an oil.

Example 15

Synthesis of 3,7,11-Trimethyl-12-[2-(2,6,10-trimethyl-undeca-1,5,9-trienyl)-[1,3]dithian-2-yl]-dodeca-2,6,10-trien-1-ol

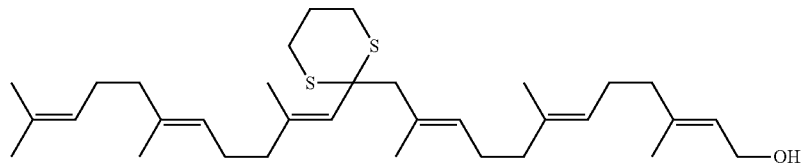 [SMILES: CC(C)=CCC/C(C)=C/CC/C(C)=C/C1(C/C(C)=C/CC/C(C)=C/CC/C(C)=C/CO)SCCCS1]

A solution of sodium methoxide (0.058 g, 0.001 mol) was prepared by carefully adding pieces of sodium metal (0.023 g) into methanol (2 ml) at 0° C. To this solution was added, drop wise, the compound (Sch.14. III) (2.5 g, 0.004 mol) dissolved in methanol (8 ml). This reaction mixture was stirred for 4 hours at which time TLC indicated the consumption of starting material. This reaction mixture was treated with 1M HCl solution to achieve a pH of 7. The methanol was removed under vacuum and the crude product was further diluted with EtOAc (60 ml). The organic layer was washed with water before separating it out. It was further treated with brine, dried over MgSO$_4$ and finally evaporated under vacuum to obtain the deacylated product (2.0 g, 94%).

Example 16

Synthesis of 3,7,11,15,19,23-Hexamethyl-tetracosa-2,6,10,14,18,22-hexaen-1-ol Deprotection of dithiane was achieved in two steps; 1) Conversion of the dithiane into a ketone; 2) Wolf-Kishner reduction of the ketone into an alkane.

1. Conversion of the dithiane into a ketone: To a 10 ml solution of the compound (Sch.14. IV) (2.0 g, 0.0037 mol) in a mixture of MeCN/CH$_2$Cl$_2$/H$_2$O (8:1:1) was added the Dess-Martin Periodinane (3.2 g, 0.0074 mol) in one portion. This reaction mixture was stirred at room temperature until the consumption of the starting material. The reaction was diluted with 50% aq. NaHCO$_3$, the layers were separated, and the aqueous layer was extracted CH$_2$Cl$_2$. The combined organic layers were washed with brine, dried over MgSO$_4$, and finally evaporated under vacuum to recover a keto analogue of compound (Sch.14. IV), which was subjected to further reaction without any purification.

2. Conversion of the ketone into an alkane: 24-Hydroxy-2,6,10,14,18,22-hexamethyl-tetracosa-2,6,10,14,18,22-hexaen-12-one (1.62 g, 0.0037 moles) and diethyleneglycol (5.0 g) were added to a three-neck 50 ml flask under nitrogen. The solution was heated to 60° C. followed by the exothermic addition of hydrazine (0.41 g, 0.007 moles) and KOH (0.21 g, 0.0037 moles). The reaction mixture was then heated to reflux (125° C.). Water from the mixture was collected in an addition funnel by opening the valve on the pressure-equalizing arm and allowing the water to evaporate and condense in the funnel. Thus the temperature slowly climbed to 215° C. over 4 hours. The mixture was cooled to ambient and diluted with water (10 ml) and toluene (6 ml). Under stirring, 1M aqueous HCl acid was gradually added to neutralize the pH to −5-6. The organic phase was separated, washed with brine, dried over MgSO$_4$ and finally concentrated under vacuum to obtain the desired hexaprenol as a thick oil (1.2 g, 77% yield over two steps). $^1$H NMR (400 MHz, CDCl$_3$) δ 5.40 (t, 1H, J=6 Hz), 5.10 (m, 5H), 4.13 (d, 2H, J=7 Hz), 2.06 (m, 20H), 1.68 (s, 11H), 1.62 (s, 10H).

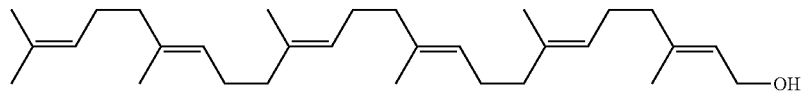

Example 17

Synthesis of 1-Bromo-3,7,11,15,19,23-hexamethyl-tetracosa-2,6,10,14,18,22-hexaene

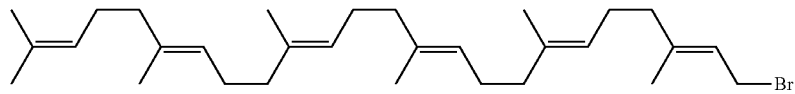 [SMILES: CC(C)=CCC/C(C)=C/CC/C(C)=C/CC/C(C)=C/CC/C(C)=C/CC/C(C)=C/CBr]

To a solution of PPh$_3$ (0.92 g, 0.0035 mol) in CH$_2$Cl$_2$ (20 ml) was added drop wise, a solution of bromine (0.553 g, 0.0035 mol) in CH$_2$Cl$_2$ (5 ml). This reaction mixture was stirred at room temperature until the formation of the triphenylphosphine-bromine complex became evident. This reaction mixture was brought to 0° C. before drop wise addition of a solution of hexaprenol (1.2 g, 0.0028 mol) dissolved in CH$_2$Cl$_2$ (10 ml). The reaction mixture was quenched by drop wise addition of cold water after ensuring the consumption of the starting material by TLC. All the contents of reaction mixture were transferred to a separatory funnel containing CH$_2$Cl$_2$ (50 ml). The organic layer was washed with saturated NaHCO$_3$ (2×10 ml) very carefully, followed by washing with water (2×10 ml). The aqueous layer was further extracted with CH$_2$Cl$_2$. The organic layer was combined, washed with brine, dried over MgSO$_4$ before evaporating the solvent under reduced pressure to yield a crude white solid which was washed with hexanes (50 ml).

The filtrate obtained was concentrated under vacuum to provide the hexaprenyl bromide (1.3 g, 94%) as yellow liquid.

Examples 18 to 20

Synthesis of Vitamin K2-7

The aromatic building block (Sch.15. I) and the hexaprenyl bromide (Sch.15. II) are reacted in the following sequence of reactions to obtain the all-trans vitamin K2-7.

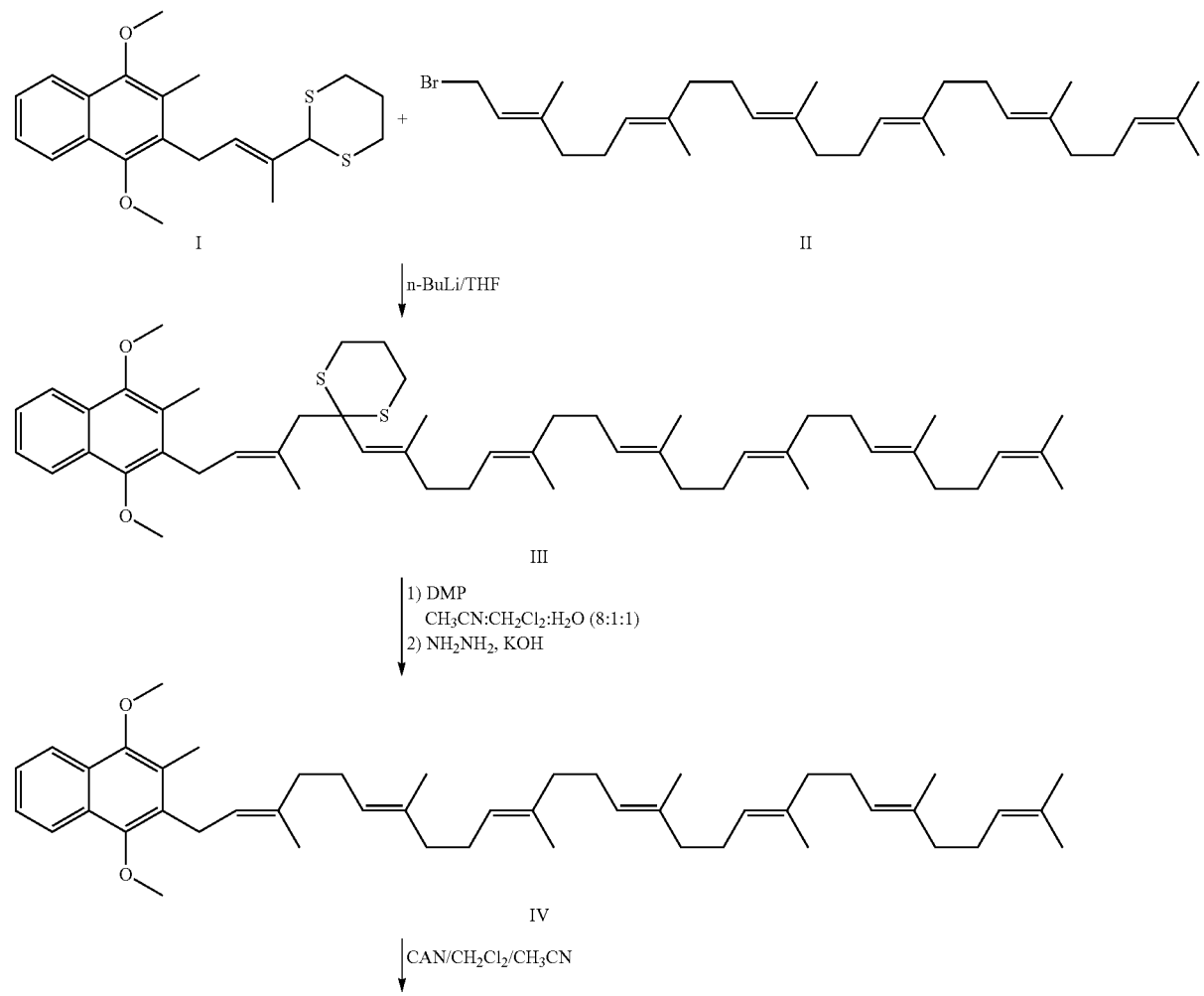

Scheme 15. Complete synthesis of vitamin K2-7.

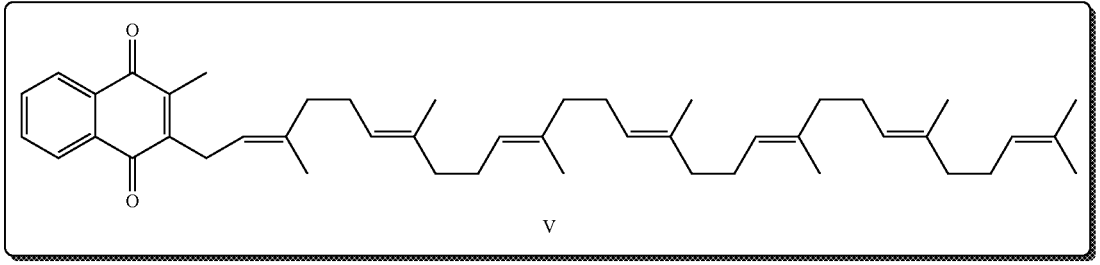

Example 18

Synthesis of 2-[4-(1,4-Dimethoxy-3-methyl-naphthalen-2-yl)-2-methyl-but-2-enyl]-2-(2,6,10,14,18,22-hexamethyl-tricosa-1,5,9,13,17,21-hexaenyl)-[1,3]dithiane

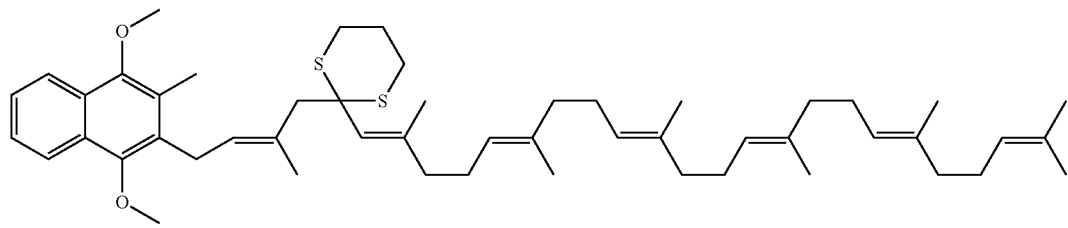 [SMILES: COc1c(C)c(C/C=C(\C)CC2(/C=C(\C)CC/C=C(\C)CC/C=C(\C)CC/C=C(\C)CC/C=C(\C)CCC=C(C)C)SCCCS2)c(OC)c2ccccc12]

To a solution of 2-[3-(1,4-Dimethoxy-3-methyl-naphthalen-2-yl)-1-methyl-propenyl]-[1,3]dithiane (Sch.15. I) (1.1 g, 0.0029 mol) in THF (20 ml) was added n-BuLi (3.3 ml, 0.003 mol), drop wise, at −78° C. under nitrogen. The resultant reaction mixture was stirred for 30 minutes before adding a solution of 1-Bromo-3,7,11,15,19,23-hexamethyl-tetracosa-2,6,10,14,18,22-hexaene (Sch.15. II) (1.47 g, 0.0030 mol) in THF (5 ml). The reaction mixture was quenched by adding saturated NH₄Cl (5 ml), after stirring for 12 hrs. All the contents of the reaction mixture were transferred to a separatory funnel containing EtOAc (100 ml). The aqueous layer was further extracted with EtOAc (2×10 ml). The organic layers were combined, washed with brine (20 ml), dried over MgSO₄, filtered and finally removed under reduced pressure to obtain the desired coupled product (Sch.15. III) as a yellow liquid (1.89 g, 83% yield) which was subjected to dithiane deprotection without any purification.

Example 19

Synthesis of 2-(3,7,11,15,19,23,27-Heptamethyl-octacosa-2,6,10,14,18,22,26-heptaenyl)-1,4-dimethoxy-3-methyl-naphthalene Deprotection of the dithiane was achieved in two steps; 1) Conversion of the dithiane into a ketone; 2) Wolf-Kishner reduction of the ketone into an alkane.

1. Conversion of the dithiane into a ketone: To a 10 ml solution of 2-[4-(1,4-Dimethoxy-3-methyl-naphthalen-2-yl)-2-methyl-but-2-enyl]-2-(2,6,10,14,18,22-hexamethyl-tricosa-1,5,9,13,17,21-hexaenyl)-[1,3]dithiane (Sch.15. III) (0.97 g, 0.0012 mol) in a mixture of MeCN/CH₂Cl₂/H₂O (8:1:1) was added Dess-Martin Periodinane (1.05 g, 0.0024 mol) in one portion. This reaction mixture was stirred at room temperature until the consumption of the starting material. The reaction was then diluted with 50% aq. NaHCO₃, the layers separated, and the aqueous layer extracted with CH₂Cl₂ (30 ml). The combined organic layers were then washed with brine, dried over MgSO₄, and finally evaporated under vacuum to recover the keto analogue of the compound (Sch.15. III) which was used for further reaction without any purification.

2. Conversion of the ketone into an alkane: 24-Hydroxy-2,6,10,14,18,22-hexamethyl-tetracosa-2,6,10,14,18,22-hexaen-12-one (0.0012 moles) and diethyleneglycol (5.0 g) were charged to a three-neck 50 ml flask under nitrogen. The solution was heated to 60° C. followed by the exothermic addition of hydrazine (0.13 g, 0.0025 moles) and KOH (0.074 g, 0.0013 moles). The reaction mixture was then heated to reflux (125° C.). Water from the mixture was collected in an addition funnel by opening the valve on the pressure-equalizing arm, allowing the water to evaporate and condense in the funnel. Thus the temperature slowly climbed to 215° C. over 4 hours. The mixture was cooled to ambient and diluted with water (10 ml) and toluene (6 ml).

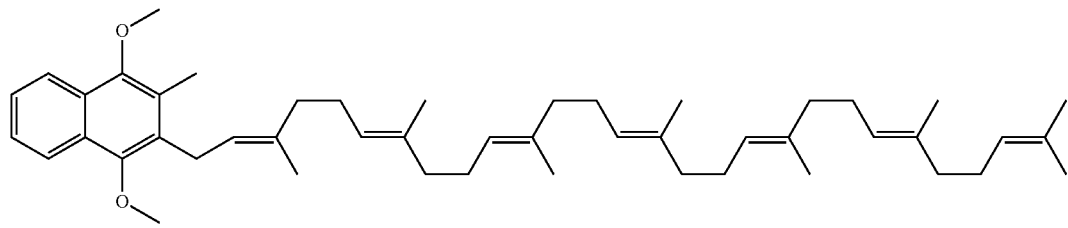 [SMILES: COc1c(C)c(C/C=C(\C)CC/C=C(\C)CC/C=C(\C)CC/C=C(\C)CC/C=C(\C)CC/C=C(\C)CCC=C(C)C)c(OC)c2ccccc12]

Under stirring, 1M aqueous HCl acid was gradually added to neutralize the pH to ~5-6. The organic phase was separated, washed with brine, dried over MgSO$_4$ and finally concentrated under vacuum to obtain the desired hexaprenol as a thick oil (0.68 g, 83% yield over two steps). $^1$H NMR (400 MHz, CDCl$_3$) δ 8.05 (m, 2H), 7.5 (m, 2H), 5.10 (m, 7H), 3.87 (s, 3H), 3.86 (s, 3H), 3.57 (d, 2H, J=7.0 Hz), 2.38 (s, 3H), 2.05 (m, 24H), 1.83 (s, 3H), 1.65 (s, 3H), 1.59 (s, 12H), 1.57 (s, 6H).

Example 20

Synthesis of Vitamin K2-7

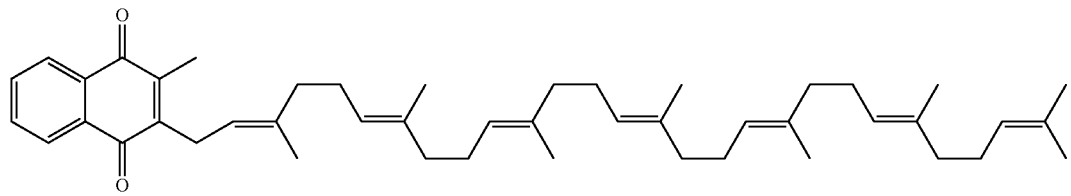 [SMILES: CC(C)=CCC/C(C)=C/CC/C(C)=C/CC/C(C)=C/CC/C(C)=C/CC/C(C)=C/CC/C(C)=C/CC1=C(C)C(=O)c2ccccc2C1=O]

To a solution of 2-(3,7,11,15,19,23,27-Heptamethyl-octacosa-2,6,10,14,18,22,26-heptaenyl)-1,4-dimethoxy-3-methyl-naphthalene (Sch.15. IV) (0.68, 0.001 mol) in acetonitrile (5 ml) was added an aqueous solution of ceric ammonium nitrate (1.1 g, 0.002 mol) portion wise over 5 min. The resultant reaction mixture was stirred at room temperature for 4 hours at which time the TLC indicated the completion of the reaction. All contents of the reaction flask were transferred to a separatory funnel containing chloroform (15 ml). The organic layer was washed with water (2×5 ml) and the aqueous layers were combined and extracted with chloroform (5 ml). The organic layers were combined, washed with brine (5 ml), dried over MgSO4, filtered and removed under vacuum to obtain vitamin K2-7 (0.52 g, 80% yield). $^1$H NMR (400 MHz, CDCl$_3$) δ 8.05 (m, 2H), 7.64 (m, 2H), 5.05 (m, 7H), 3.35 (d, 2H, J=7.0 Hz), 2.16 (s, 3H), 2.05 (m, 24H), 1.77 (s, 3H), 1.65 (s, 3H), 1.57 (s, 12H), 1.53 (s, 6H).

We claim:

1. A method for synthesis of polyprenylated quinone derivatives comprising regiospecific and stereospecific synthesis of compound of formula I

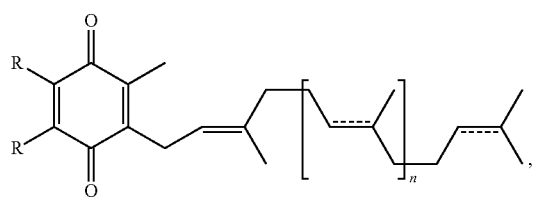

wherein n=an integer from 0 to 8,
R=is independently selected from —CH=CH—CH=CH—, wherein both R groups form a naphthalene ring and OCH3; and
the said method comprising the steps of providing a dithioacetal derivative selected from the group of quinones (II), prenols (V) and combinations thereof,

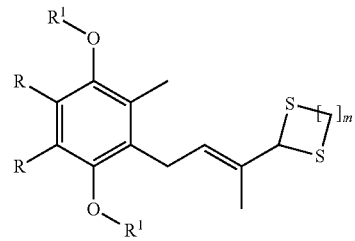

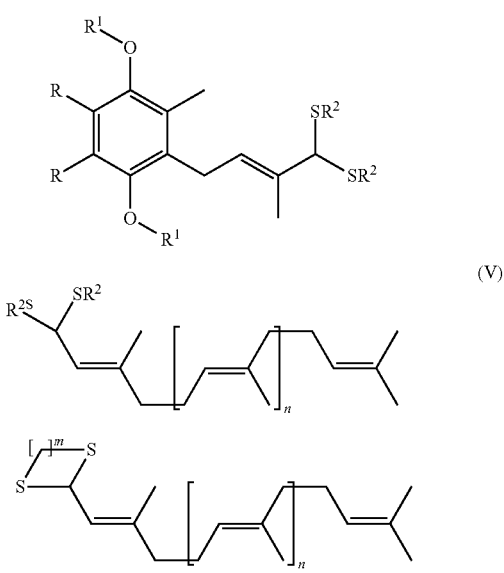

wherein m=2 or 3;
n=is an integer from 0 to 8;
R=—CH=CH—CH=CH—, wherein both R groups form a naphthalene ring or OCH$_3$
R$^1$=CH$_2$OCH$_3$, TMS, TBS, Acetyl, Benzyl, or PMB; and
R$^2$=Et or Ph;
the said derivatives participating in a reaction with halides of respective counter synthon of formula III or IV,

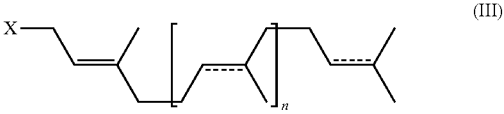

-continued
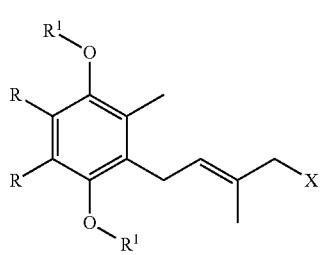
(IV)
wherein R=—CH=CH—CH=CH—, wherein both R groups form a naphthalene ring or OCH$_3$;
R$^1$=CH$_2$OCH$_3$, TMS, TBS, Acetyl, Benzyl, or PMB; and
X=OMs, Br, Cl, I, OTs.
2. The method of claim 1 wherein the said quinone derivatives are selected from the group consisting of coenzyme Q10, vitamin K1, vitamins K2-4, K2-6, K2-7, K2-8 and K2-9.
* * * * *